(12) United States Patent
Svendsen et al.

(10) Patent No.: US 8,211,631 B2
(45) Date of Patent: Jul. 3, 2012

(54) IN VITRO MODEL OF SPINAL MUSCULAR ATROPHY

(75) Inventors: Clive Svendsen, Los Angeles, CA (US); Allison Ebert, Fitchburg, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 45 days.

(21) Appl. No.: 12/653,932

(22) Filed: Dec. 18, 2009

(65) Prior Publication Data
US 2010/0279893 A1 Nov. 4, 2010

Related U.S. Application Data

(60) Provisional application No. 61/138,853, filed on Dec. 18, 2008.

(51) Int. Cl.
*C12Q 1/02* (2006.01)
*G01N 33/53* (2006.01)
*C12N 15/00* (2006.01)
*C12N 15/86* (2006.01)
*C12N 5/079* (2010.01)
*C12N 5/0793* (2010.01)
*C12N 5/0797* (2010.01)
*C12N 5/10* (2006.01)

(52) U.S. Cl. ............. 435/4; 435/7.1; 435/440; 435/455; 435/456; 435/465; 435/325; 435/368; 435/371; 435/377

(58) Field of Classification Search ........................ None
See application file for complete search history.

(56) References Cited

OTHER PUBLICATIONS

Marchetto et al., Human Molecular Genetics, vol. 19, Review Issue 1, 2010, pp. R71-R76.*
Bolstad, B. M. et al., A comparison of normalization methods for high density oligonucleotide array data based on variance and bias, Bioinformatics 19, 185-193, 2003.
Brichta, L. et al., Valproic acid increases the SMN2 protein level: a well-known drug as a potential therapy for spinal muscular atrophy, Hum. Mol. Genet. 12, 2481-2489, 2003.
Bromberg, M. B. et al., Motor unit number estimation in infants and children with spinal muscular atrophy, Muscle & Nerve 25:445-447, 2002.
Carrel, T. L. et al., Survival motor neuron function in motor axons is independent of functions required for small nuclear ribonucleoprotein biogenesis. J. Neurosci. 26, 11014-11022, 2006.
Carriedo, S. G. et al., Motor neurons are selectively vulnerable to AMPA/kainate receptor-mediated injury in vitro, J. Neurosci. 16, 4069-4079, 1996.
Chan, E. M. et al., Live cell imaging distinguishes bona fide human iPS cells from partially reprogrammed cells, Nat. Biotech., 27, 1033-1037, 2009.
Ciccolini, F. et al., Fibroblast growth factor 2 (FFG-2) promotes acquisition of epidermal growth factor (EGF) responsiveness in mouse striatal precursor cells: identification of neural precursors responding to both EGF and FGF-2, J. Neurosci. Res., 18, 7869-7880,1998.
Coovert, D. D. et al., The survival motor neuron protein in spinal muscular atrophy, Hum. Mol. Genet. 6, 1205-1214, 1997.
Crawford, T. O. et al., The neurobiology of childhood spinal muscular atrophy, Neurobiol. Dis. 3, 97-110, 1996.
Didonato, C. J. et al., Cloning, Characterization, and Copy Number of the Murine Survival Motor Neuron Gene: Homolog of the Spinal Muscular Atrophy-Determining Gene, Genome Res. 7, 339-352, 1997.
Dimos, J. T. et al., Induced Pluripotent Stem Cells Generated from Patients with ALS Can Be Differentiated into Motor Neurons, Science 321, 1218-1221, 2008.
Fischer, U. et al., The SMN-SIP1 complex has an essential role in spliceosomal snRNP biogenesis, Cell 90, 1023-1029, 1997.
Fox, V. et al., Cell-cell signaling through NOTCH regulates human embryonic stem cell proliferation, Stem Cells 26, 715-723, 2008.
Gavrilov, D. K. et al., Differential SMN2 expression associated with SMA severity, Nature Genet. 20, 230-231, 1998.
Guo, G. et al., Klf4 reverts developmentally programmed restriction of ground state pluripotency, Development 136, 1063-1069, 2009.
Hsieh-Li, H. M. et al., A mouse model for spinal muscular atrophy, Nature Genet. 24, 66-70, 2000.
Irizarry, R. A. et al., Exploration, normalization, and summaries of high density oligonucleotide array probe level data, Biostatistics 4, 249-264, 2003.
Jaenisch, R. et al., Stem cells, the molecular circuitry of pluripotency and nuclear reprogramming, Cell 132, 567-582, 2008.
Jakel, R. J. et al., Using human neural stem cells to model neurological disease, Nature Rev. Genet. 5, 136-144, 2004.
Jessell, T. M., Neuronal specification in the spinal cord: Inductive signals and transcriptional codes, Nature Rev. Genet. 1, 20-29, 2000.
Kaji, K. et al., Virus-free induction of pluripotency and subsequent excision of reprogramming factors, Nature, 458, 771-775, 2009.
Le, T. T. et al., SMN-Delta-7, the major product of the centromeric survival motor neuron (SMN2) gene, extends survival in mice with spinal muscular atrophy and associates with full-length SMN, Hum. Mol. Genet. 14, 845-857, 2005.
Lefebvre, S. et al., Identification and characterization of a spinal muscular atrophy-determining gene, Cell 80, 155-165,1995.
Lendahl, U. et al., CNS stem cells express a new class of intermediate filament protein, Cell 60, 585-595; 1990.

(Continued)

*Primary Examiner* — Jeffrey Stucker
*Assistant Examiner* — Stephen Gucker
(74) *Attorney, Agent, or Firm* — Quarles & Brady, LLP

(57) ABSTRACT

A population of iPS cells derived from somatic cells from a spinal muscular atrophy patient is disclosed. In one embodiment of the invention, the cells have been cultured to produce neural cells. In another embodiment, the invention is a method of testing compounds for their ability to modify cellular SMN levels comprising the steps of obtaining a population of iPS cells derived from a spinal muscular atrophy patient or cells derived from the iPS cells, and examining the effect of a test compound on SMN levels.

8 Claims, 30 Drawing Sheets
(15 of 30 Drawing Sheet(s) Filed in Color)

OTHER PUBLICATIONS

Li, X. J. et al., Specification of motoneurons from human embryonic stem cells, Nature Biotechnol. 23, 215-221, 2005.

Liu, Q. et al., The spinal muscular atrophy disease gene product, SMN, and its associated protein SIP1 are in a complex with spliceosomal snRNP proteins, Cell 90, 1013-1021, 1997.

Loh, Y. et al., Generation of induced pluripotent stem cells from human blood, Blood, 113, 5476-5479, 2009.

Lorson, C. L. et al., SMN oligomerization defect correlates with spinal muscular atrophy severity, Nat. Gen. 19, 63-66, 1998.

Lorson, M. A. et al., Identification and characterization of the porcine (*Sus scrota*) survival motor neuron (SMN1) gene: an animal model for therapeutic studies, Dev. Dyn., 237, 2268-2278, 2008.

Lowry, W. E. et al., Generation of human induced pluripotent stem cells from dermal fibroblasts, Proc. Natl. Acad. Sci. USA 105, 2883-2888, 2008.

Mattis, V. B. et al., Novel aminoglycosides increase SMN levels in spinal muscular atrophy fibroblasts, Hum. Genet. 120, 589-601, 2006.

Monani, U. R. et al., The human centromeric survival motor neuron gene (SMN2) rescues embryonic lethality in Smn-/- mice and results in a mouse with spinal muscular atrophy, Hum. Mol. Genet. 9, 333-339, 2000.

Monani, U. R., Spinal muscular atrophy: a deficiency in a ubiquitous protein; a motor neuron-specific disease, Neuron 48, 885-896, 2005.

Munsat, T. L. et al., Meeting Report, International SMA consortium meeting, Jun. 26-28, 1992, Bonn, Germany, Neuromusc. Disord. 2, 423-428, 1992.

Park, I. H. et al., Disease-specific induced pluripotent stem cells, Cell 134, 877-886, 2008.

Park, I. H. et al., Reprogramming of human somatic cells to pluripotency with defined factors, Nature, 451, 141-146, 2008.

Pellizzoni, L. et al., Essential role for the SMN complex in the specificity of snRNP assembly, Science 298, 1775-1779, 2002.

Schmid, A. et al., Animal models of spinal muscular atrophy, J. Child Neurol. 22, 1004-1012, 2007.

Schrank, B. et al., Inactivation of the survival motor neuron gene, a candidate gene for human spinal muscular atrophy, leads to massive cell death in early mouse embryos, Proc. Natl. Acad. Sci. USA 94, 9920-9925, 1997.

Shi, Y. et al., Induction of pluripotent stem cells from mouse embryonic fibroblasts by Oct4 and Klf4 with small-molecule compounds, Cell Stem Cell 3, 568-574, 2008.

Shi, Y. et al., A combined chemical and genetic approach for the generation of induced pluripotent stem cells, Cell Stem Cell 2, 525-528, 2008.

Sumner, C. J. et al., Valproic acid increases SMN levels in spinal muscular atrophy patient cells, Ann. Neurol. 54, 647-654, 2003.

Sumner, C. J. et al., SMN mRNA and protein levels in peripheral blood: biomarkers for Sma clinical trials, Neurology 66, 1067-1073, 2006.

Suzuki, R. et al., Pvclust: an R package for assessing the uncertainty in hierarchical clustering, Bioinformatics 22, 1540-1542, 2006.

Svendsen, C. N. et al., A new method for the rapid and long term growth of human neural precursor cells, J. Neurosci. Methods 85, 141-152, 1998.

Takahashi, K. et al., Induction of pluripotent stem cells from adult human fibroblasts by defined factors, Cell, 131, 861-872, 2007.

Thomson, J. A. et al., Embryonic stem cell lines derived from human blastocysts, Science, 282, 1145-1147, 1998.

Wehner, K. A. et al., Survival motor neuron protein in the nucleolus of mammalian neurons, Brain Res. 945, 160-173, 2002.

Wichterle, H. et al., Directed differentiation of embryonic stem cells into motor neurons, Cell 110, 385-397, 2002.

Wolstencroft, E. C. et al., A non-sequence-specific requirement for SMN protein activity: the role of aminoglycosides in inducing elevated SMN protein levels, Hum. Mol. Genet. 14, 1199-1210, 2005.

Lee et al., "Modelling pathogenesis and treatment of familial dysautonomia using patient-specific iPSCs." Nature 461:402-406; 2009.

Liu et al., "Recapitulation of premature ageing with iPSCs from Hutchinson—Gilford progeria syndrome." Nature 472:221-225; 2011.

Marchetto et al., "A Model for Neural Development and Treatment of Rett Syndrome Using Human Induced Pluripotent Stem Cells." Cell 143:527-539; 2010.

Nguyen et al., "LRRK2 Mutant iPSC-Derived DA Neurons Demonstrate Increased Susceptibility to Oxidative Stress." Cell Stem Cell 8:267-280; 2011.

Zhang et al., "Characterization of Human Huntington's Disease Cell Model from Induced Pluripotent Stem Cells." PLoS Curr 2:RRN1193; 2010.

Woltjen, K. et al., piggyBac transposition reprograms fibroblasts to induced pluripotent stem cells, Nature, 458, 766-770, 2009.

Yu, J. et al., Induced pluripotent stem cell lines derived from human somatic cells, Science 318, 1917-1920, 2007.

Zhang, H. et al., Multiprotein complexes of the survival of motor neuron protein SMN with gemins traffic to neuronal processes and growth cones of motor neurons, J. Neurosci. 26, 8622-8632; 2006.

Zhou, H. et al., Generation of induced pluripotent stem cells using recombinant proteins, Cell Stem Cell, 4, 381-384; 2009.

\* cited by examiner

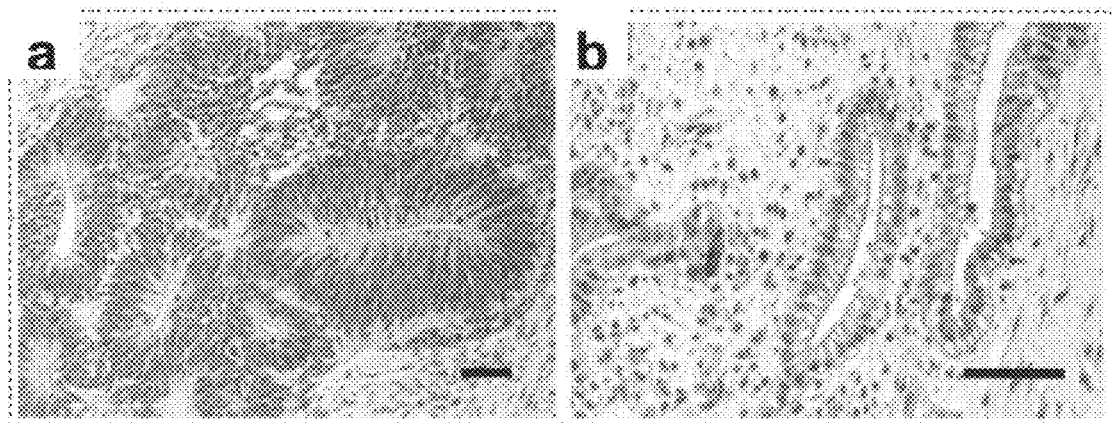
FIG. 4a, b

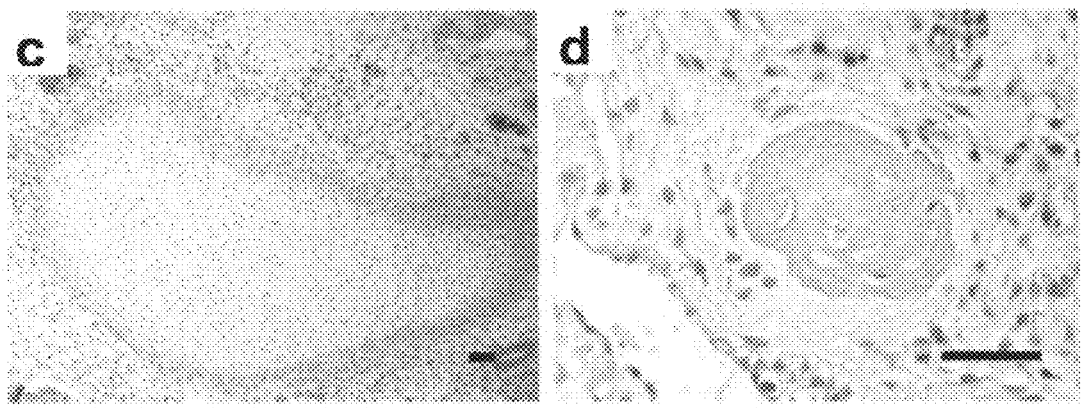
FIG. 4c, d

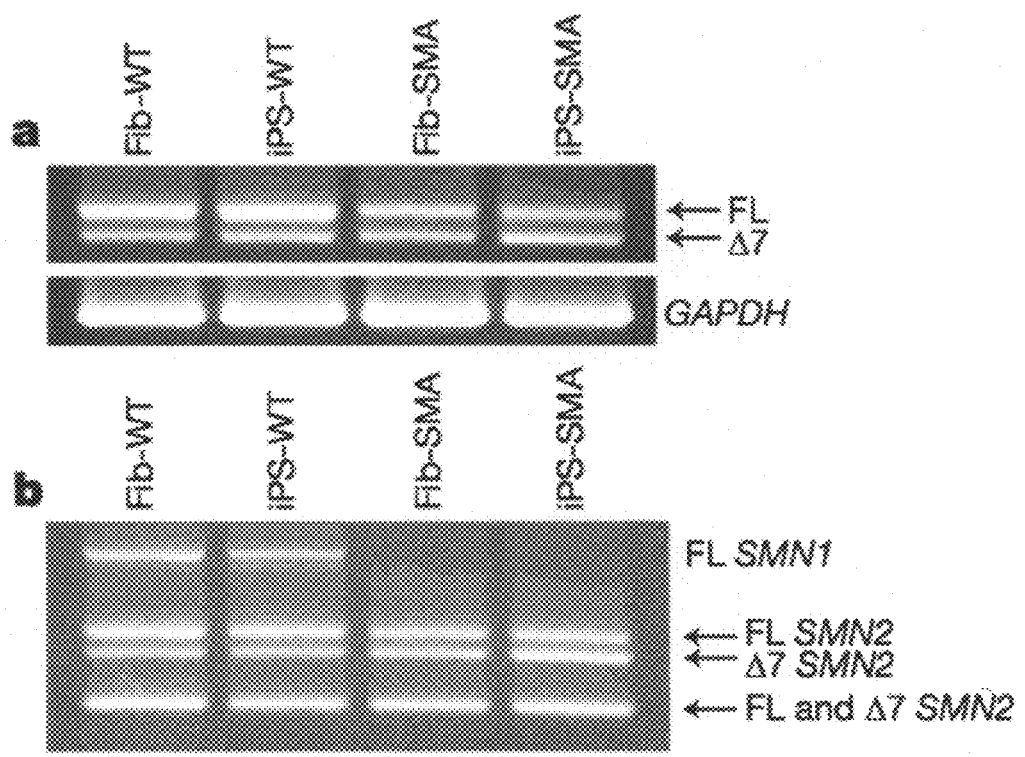
FIG. 9a, b

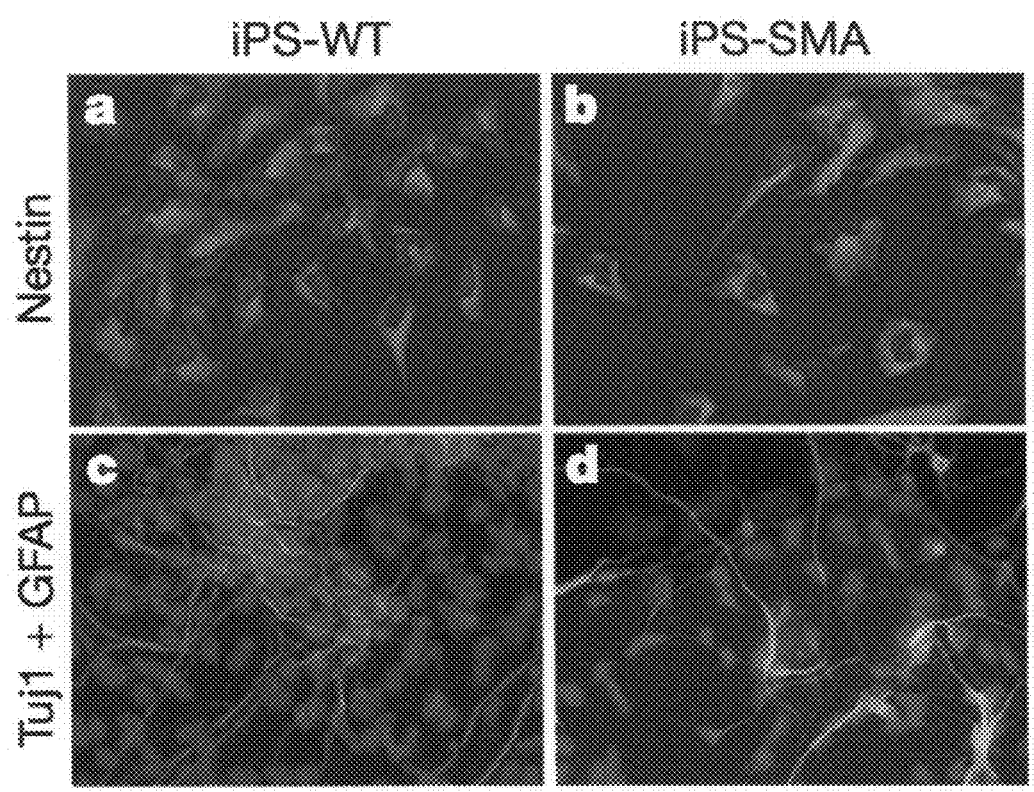
FIG. 10a-d

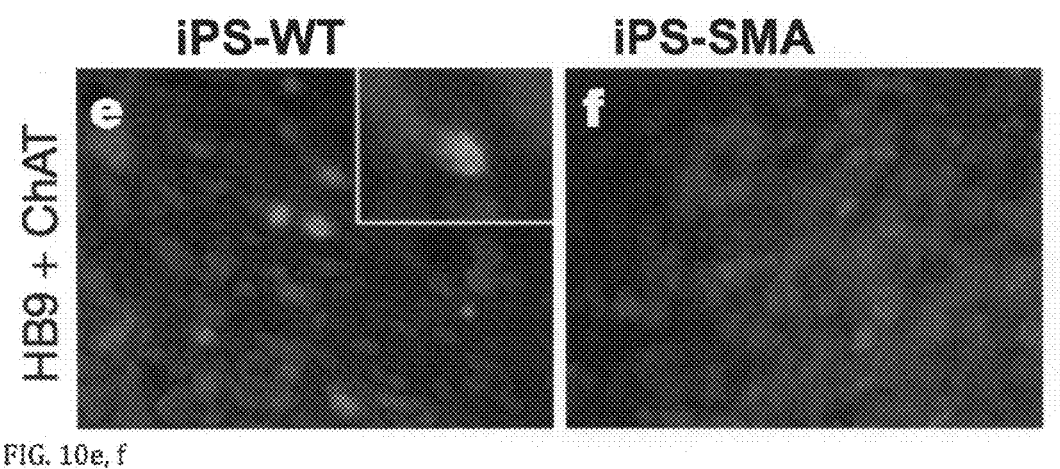
FIG. 10e, f

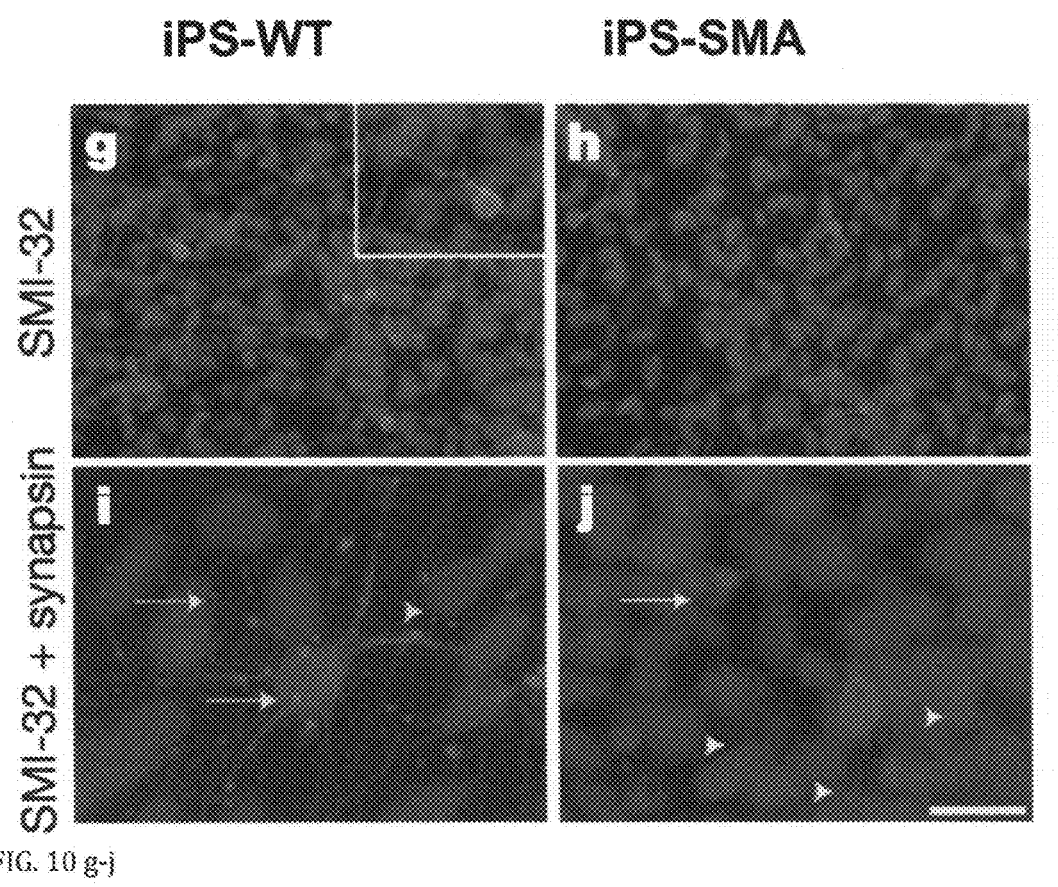
FIG. 10 g-j

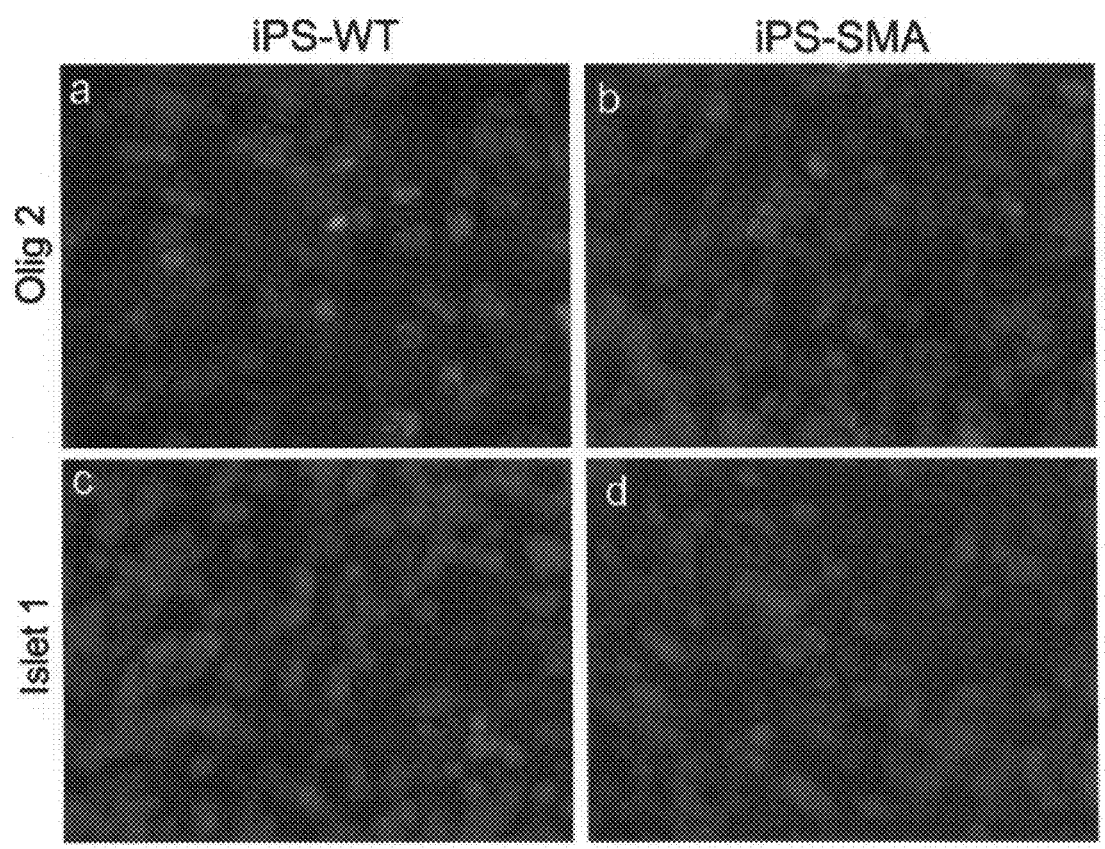
FIG. 11a-d

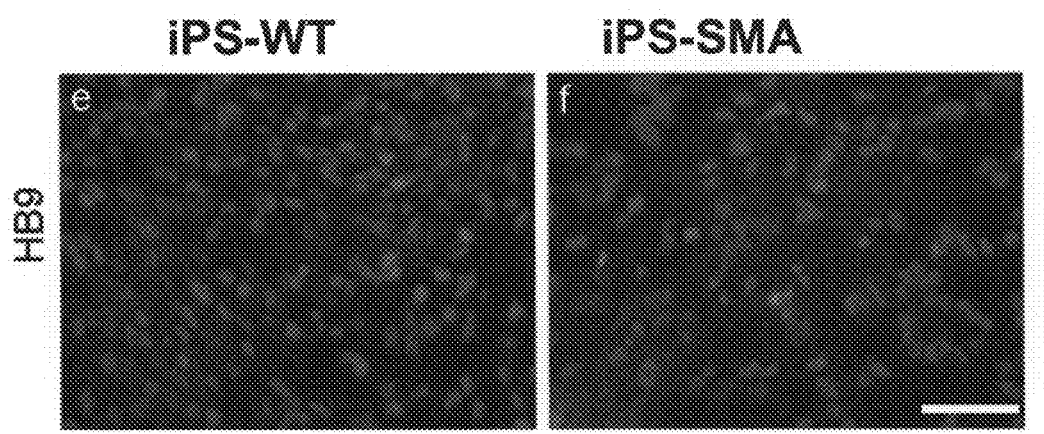
FIG. 11e, f

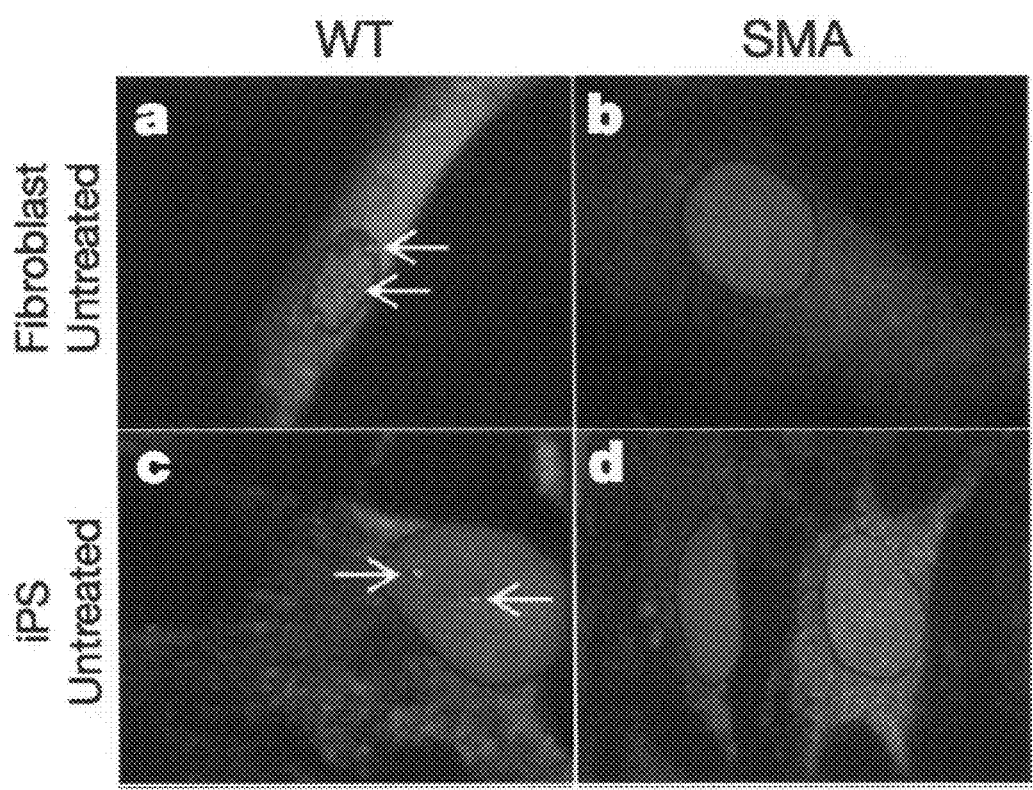
FIG. 13a-d

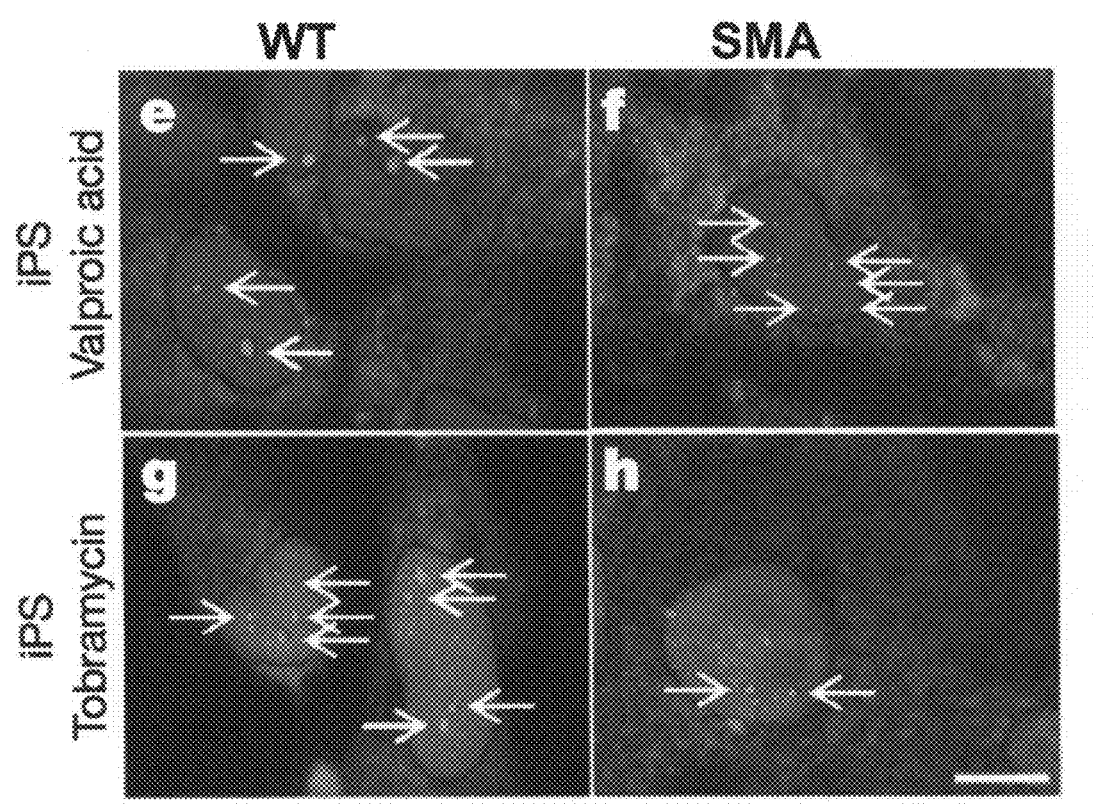
FIG 13e-h

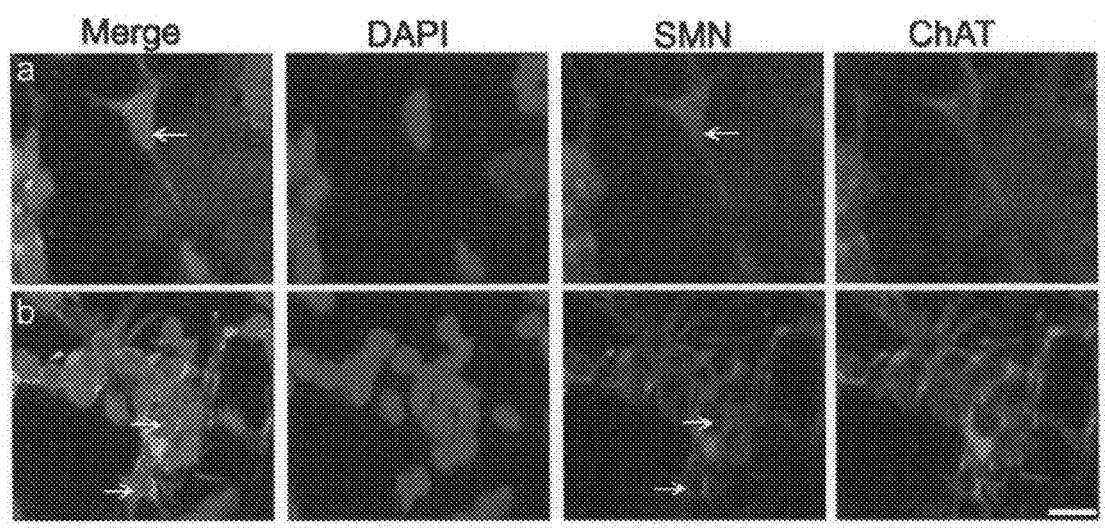
FIG. 14a, b

SEQUENCE LISTING

```
<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
gtggacctga cctgccgtct                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
ggaggagtgg gtgtcgctgt                                                   20

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 3
cagtgcccga aacccacac                                                    19

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ggagacccag cagcctcaaa                                                   20

<210> SEQ ID NO 5
<211> LENGTH: 20
<212> TYPE: DNA
<213> ORGANISM: Artificial Sequence
<220> FEATURE:
```

<223> OTHER INFORMATION: Synthetic oligonucleotide

<400> SEQUENCE: 5
agtttgtgcc agggttttg                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
acttcacctt ccctccaacc                                                   20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
tttggaagct gctggggaag                                                   20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
gatgggagga ggggagagga                                                   20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
cagaaggcct cagcacctac                                                   20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
attgttccag gtctggttgc                                                   20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
tacctcttcc tcccactcca                                                   20

<210> SEQ ID NO 12

```
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
ggtagtgctg ggacatgtga                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
agtctccaag cgacgaaaaa                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
tttcacgttt gcaactgtcc                                                 20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
aagcgcagat caaaaggaga                                                 20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16
ctgatgctct ggcagaagtg                                                 20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
agtggcctgg atagggaagt                                                 20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
```
cttggctcca tgaatctggt                                               20

<210> SEQ ID NO 19
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 19
caaaaagaag gaaggtgctc acatt                                         25

<210> SEQ ID NO 20
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 20
gtgtcattta gtgctgctct atgc                                          24

<210> SEQ ID NO 21
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 21
catggtacat gagtggctat catactg                                       27

<210> SEQ ID NO 22
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 22
tggtgtcatt tagtgctgct ctatg                                         25

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23
gcaaagagcc cgtcgtctac                                               20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
cgtgtcaggt agcggttgta                                               20

IN VITRO MODEL OF SPINAL MUSCULAR ATROPHY

CROSS-REFERENCE TO RELATED APPLICATIONS

This application claims priority to Provisional Patent Application No. 61/138,853 filed Dec. 18, 2008, the entirety of which is hereby incorporated by reference herein.

BACKGROUND OF THE INVENTION

Spinal muscular atrophy (SMA) is an autosomal recessive genetic disorder caused by mutations in the survival motor neuron 1 gene (SMN1) significantly reducing SMN protein expression (Lefebvre, S. et al. Identification and characterization of a spinal muscular atrophy-determining gene, Cell 80, 155-165, 1995; Coovert, D. D. et al. The survival motor neuron protein in spinal muscular atrophy Hum. Mol. Genet. 6, 1205-1214, 1997) and resulting in the selective degeneration of lower a-motor neurons (Crawford, T. O. & Pardo, C. A. The neurobiology of childhood spinal muscular atrophy, Neurobiol. Dis. 3, 97-110, 1996). Clinically, patients with SMA 1 typically show symptoms at 6 months of age and die by age 2 (Munsat, T. L. & Davies, K. E. International SMA consortium meeting, 26-28 Jun. 1992, Bonn, Germany, Neuromuscul. Disord. 2, 423-428, 1992).

The SMN2 gene is almost identical to SMN1 except that SMN2 has a single nucleotide difference that results in only 10% of the full-length protein being produced and high levels of a truncated, unstable protein lacking exon 7 (SMNΔ7). However, patients with several copies of SMN2 produce more full-length protein and have a less severe phenotype.

The nomenclature "SMA Type 1" is related to the copy number of SMN2 gene. All SMA patients have 100% knockdown of the SMN1 gene. A copy of the gene that only produces 10% normal protein is a modifier gene. Children with only one copy of the SMN2 gene have the most severe form of the disease (Type 1 SMA). (Children with no copies of the SMN2 gene do not survive.) As the copy number of the SMN2 gene increases, the severity of the disease decreases because the patient has more functional SMN protein. In general, SMA Type II patients typically have two copies of the SMN2 gene and Type III and IV have three and four copies respectively of the gene, although this is not absolute.

Although current model systems using worms, flies or mice have provided invaluable data concerning the genetic cause of SMA, the mechanisms of motor neuron death and potential drug therapies (Schmid, A. & DiDonato, C. J. Animal models of spinal muscular atrophy J. Child Neurol. 22, 1004-1012, 2007), they have important limitations. For example, mice, flies and worms lack the SMN2 gene and, thus, animal models require complicated knockout and overexpression strategies (Schrank, B. et al., Proc. Natl Acad. Sci. USA 94, 9920-9925, 1997; DiDonato, C. J. et al., Genome Res. 7, 339-352, 1997; Hsieh-Li, H. M. et al., Nature Genet. 24, 66-70, 2000; Monani, U. R. et al., Hum. Mol. Genet. 9, 333-339, 2000; Le, T. T. et al. SMNΔ7, gene, Hum. Mol. Genet. 14, 845-857, 2005).

As some therapies aim to target activation of endogenous SMN2 as a potential disease modifier, a human cell-based assay system would be very beneficial. Although SMA patient fibroblasts are available for study, fibroblasts do not show the same vulnerability as motor neurons, and the processing and functioning of the SMN protein probably has unique features in a neural context that is highly relevant for understanding disease mechanisms.

Induced pluripotent stem (iPS) cells, which show marked similarities to embryonic stem cells, can now be derived from human adult somatic tissues (Park, I. H. et al., Nature 451, 141-146, 2008; Jaenisch, R. & Young, R., Cell 132, 567-582, 2008; Takahashi, K. et al., Cell 131, 861-872, 2007; Yu, J. et al., Science 318, 1917-1920, 2007; Lowry, W. E. et al., Proc. Natl. Acad. Sci. USA 105, 2883-2888, 2008), and recent studies have been successful in generating patient-specific iPS cells from a variety of diseases including amyotrophic lateral sclerosis, muscular dystrophy and Huntington's disease (Dimos, J. T. et al., Science 321, 1218-1221, 2008; Park, I. H. et al., Cell 134, 877-886, 2008). None of these reports, however, has shown any disease-specific changes in cell survival or function.

BRIEF SUMMARY OF THE INVENTION

In the Examples disclosed below, we successfully established iPS cells from a type 1 SMA patient and his unaffected mother and showed that the SMA-patient-derived iPS cells retained the capacity to generate differentiated neural tissue and motor neurons while maintaining a lack of SMN1 expression and the disease phenotype of selective motor neuron death. These cells also responded to compounds known to increase SMN protein. Together, these results will allow disease modeling and drug screening for SMA in a far more relevant system (see Jakel, R. J., Schneider, B. L. & Svendsen, C. N., Nature Rev. Genet. 5, 136-144, 2004, a global review of using hES cells for modeling human disease).

In one embodiment, the present invention is a population of iPS cells derived from somatic cells from a spinal muscular atrophy patient. Preferably, the cells have the SMA 1 disease genotype and are capable of differentiation into motor neurons that maintain an SMA disease genotype and phenotype. Preferably, the cells are capable of expansion in culture characteristic of iPS cells.

In another embodiment, the cells have been cultured to produce neural cells. Preferably, the cells are Tuj1-positive neurons. In one embodiment, the cells are G FAP-positive astrocytes. In another embodiment, the cells are positive for SMN1-32 and ChAT staining.

In another embodiment, the invention is a method of testing compounds for their ability to modify cellular SMN levels. In one embodiment, the method comprising the steps of (a) obtaining a population of iPS cells derived from somatic cells from a spinal muscular atrophy patient or cells derived from the iPS cells; and (b) examining the effect of a test compound on SMN levels, wherein an increase in SMN protein relative to iPS cells derived from somatic cells from a spinal muscular atrophy patient or cells derived from the iPS cells that have not been exposed to the test compound, indicates that the compound modifies cellular SMN levels. In one embodiment, the method further comprises the step of culturing the cells of step (a) into neurons before exposure to the test compound, wherein the neurons have an SMN protein level similar (+/−10%) to a spinal muscular atrophy patient.

DESCRIPTION OF FIGURES

The patent or application file contains at least one drawing executed in color. Copies of this patent or patent application publication with color drawing(s) will be provided by the Office upon request and payment of the necessary fee.

0.8 reduced) when compared to wild-type cultures (*P<0.001, Student's t-test). Data are presented as mean+/−s.e.m.

Figure 2:
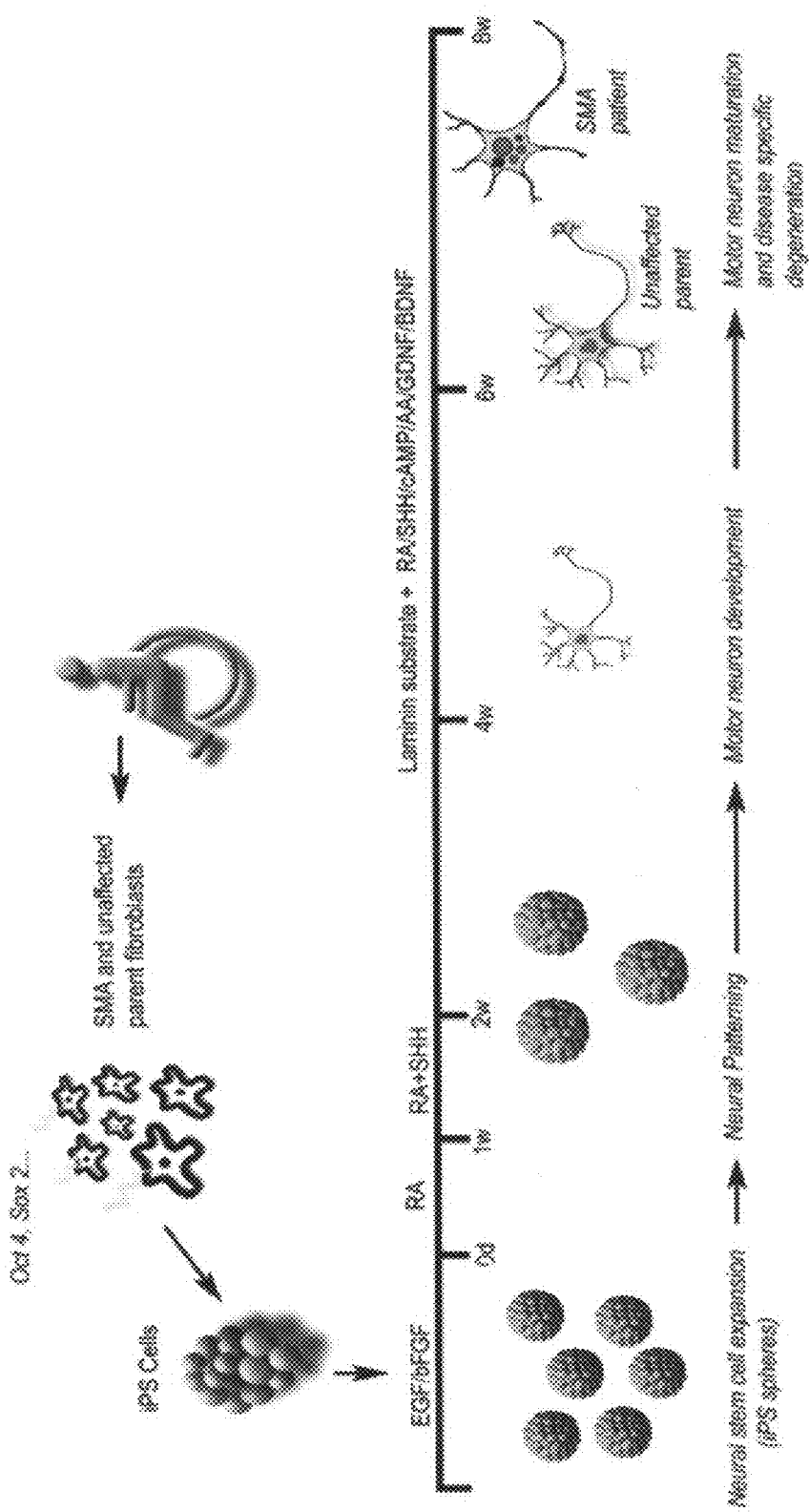

FIG. 2, The schematic depicts the induction and differentiation process of iPS cells. Following lentiviral transduction of the pluripotency genes, iPS colonies were generated, expanded, and pushed toward the neural lineage. Motor neurons derived from iPS-SMA cells showed specific loss with longer time in culture.

Figure 3A:
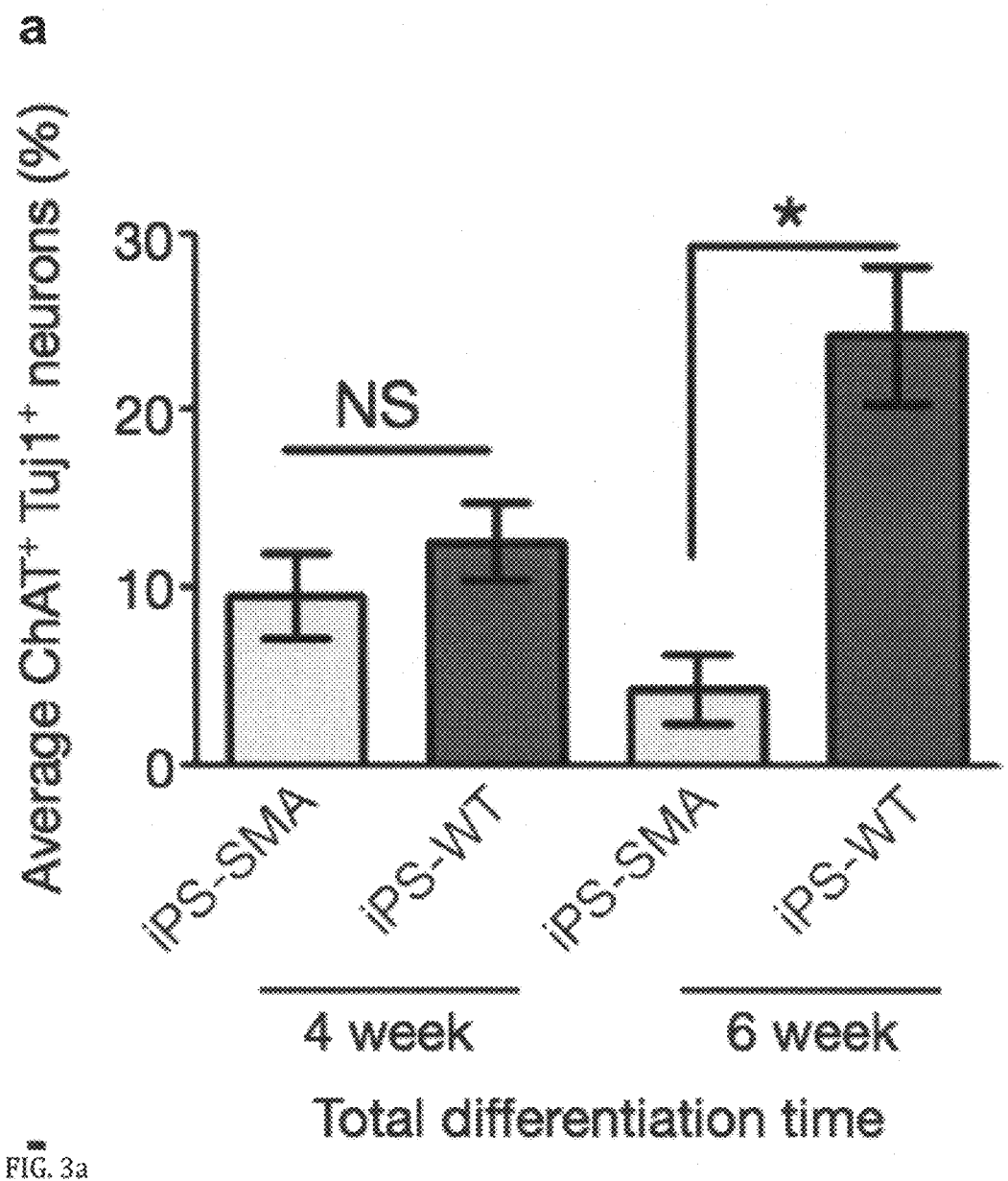
Figure 3B:
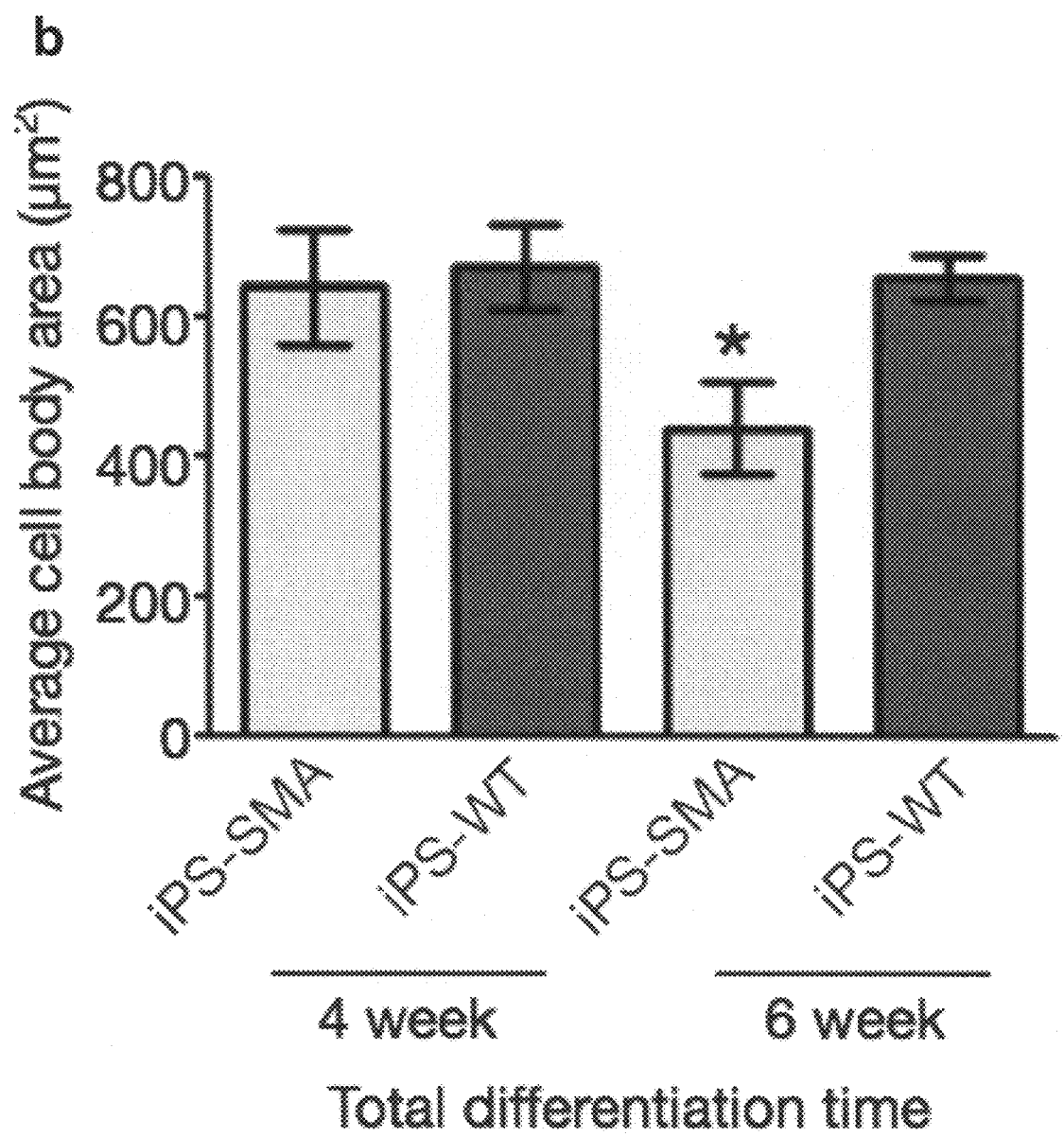
Figure 4E:
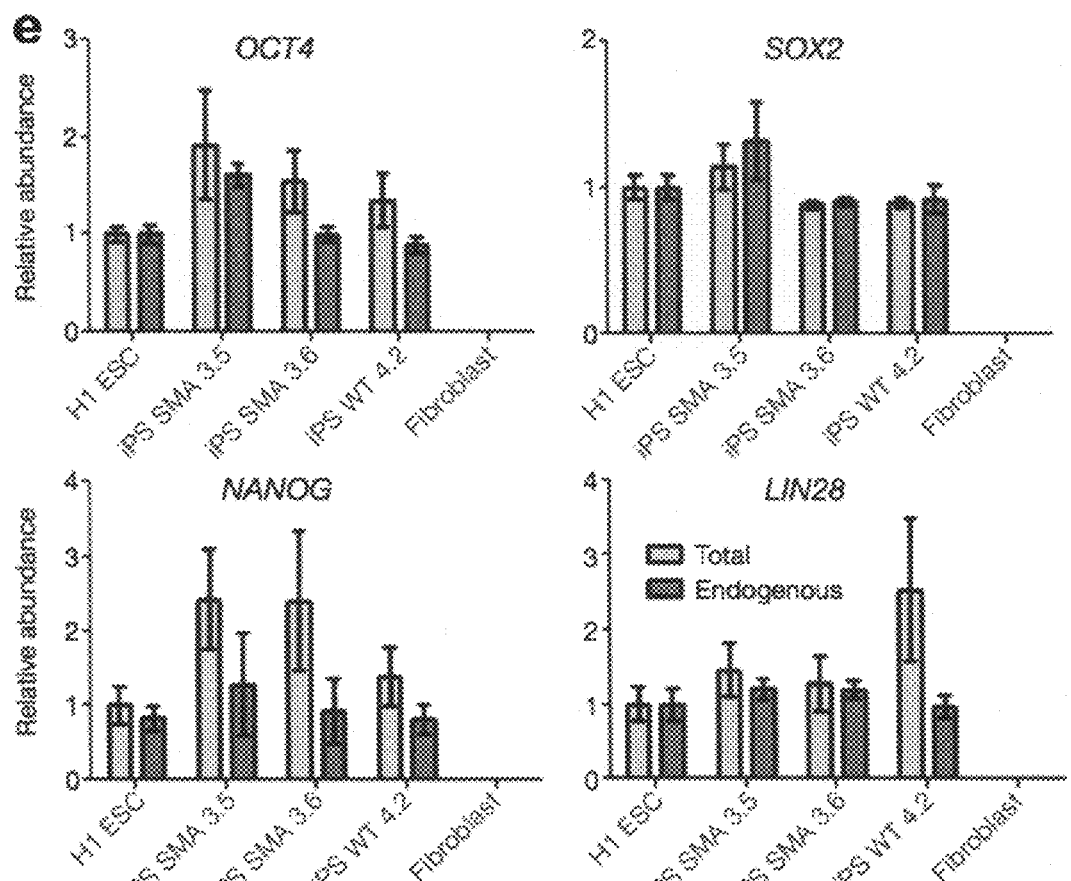

FIG. 3A, B, iPS-SMA-derived motor neurons are significantly reduced in number and size at 6 weeks compared to iPS-WT cells (n=3, *P<0.05, analysis of variance (ANOVA)). All data are presented as mean+/−s.e.m.

FIG. 4A-E, Newly generated iPS cells were fully reprogrammed. After transplantation, all iPS cells generated teratomas showing FIG. 4A neural tissue (ectoderm), FIG. 4B primitive gut (endoderm), FIG. 4C cartilage (mesoderm), and FIG. 4D bone (mesoderm). FIG. 4F, qRT-PCR showed induction of endogenous transcripts of OCT4, SOX2, NANOG and LIN28. 'Endogenous' refers to primers recognizing the 3' untranslated region, whereas 'total' identifies both the endogenous and exogenously expressed transgene. ESC, embryonic stem cells. Data are expressed as mean+/−s.e.m. Scale bars=50 mm.

Figure 5:
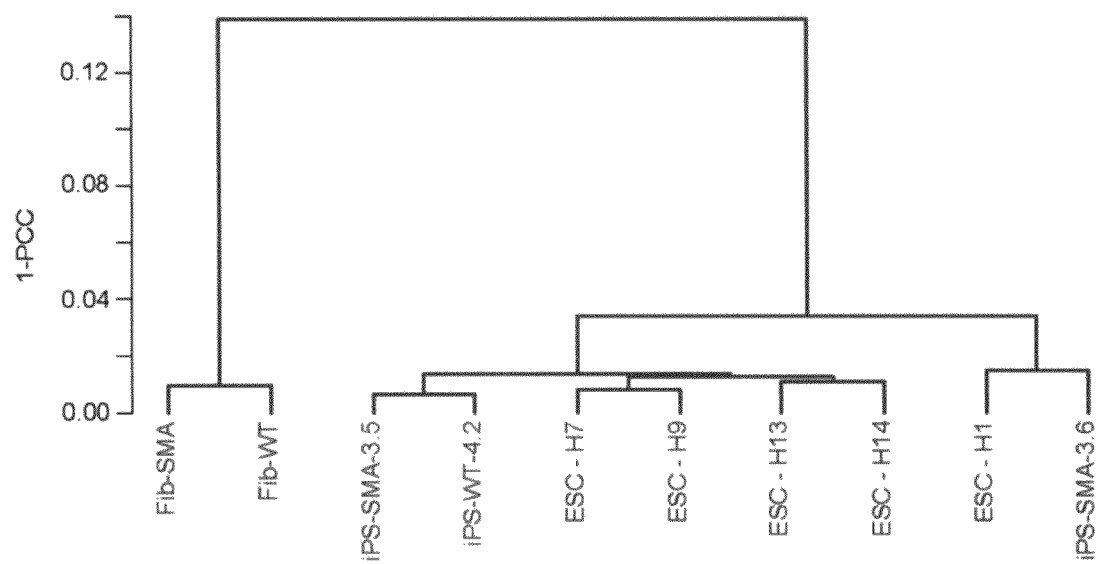

FIG. 5, Global gene expression analyses of iPS cells. Pearson correlation analyses of global gene expression (51,337 transcripts) in iPS-SMA-3.5 [p16(3)], iPS-WT-4.2 [p18(3)], Fib-SMA (p10), Fib-WT (p11), H1 [p42(12)], H7 [p73(3)], H9 [p50(5)], H13 [p43(5)] and H14 [p61(5)] ES cells. 1-PCC, Pearson Correlation Coefficient.

Figure 6:
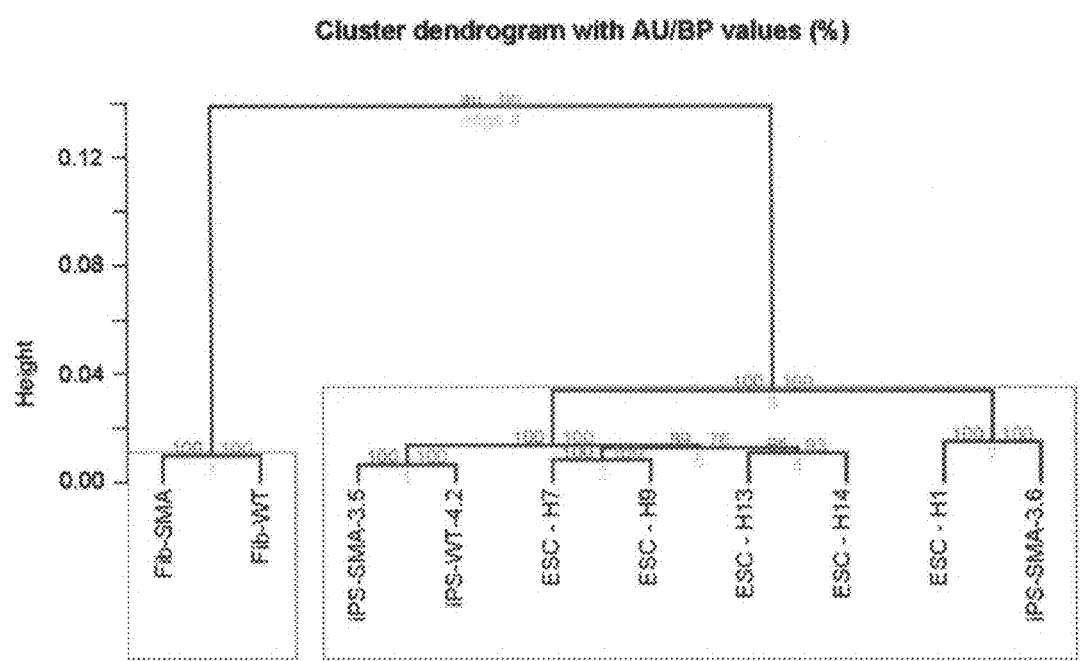

FIG. 6. Multiscale bootstrap resampling (10,000 bootstraps) of the hierachical clustering. Assessment of ten samples verified the certainty of cluster existence. AU: approximately unbiased p-value; BP: bootstrap probabilities.

Figure 7A:
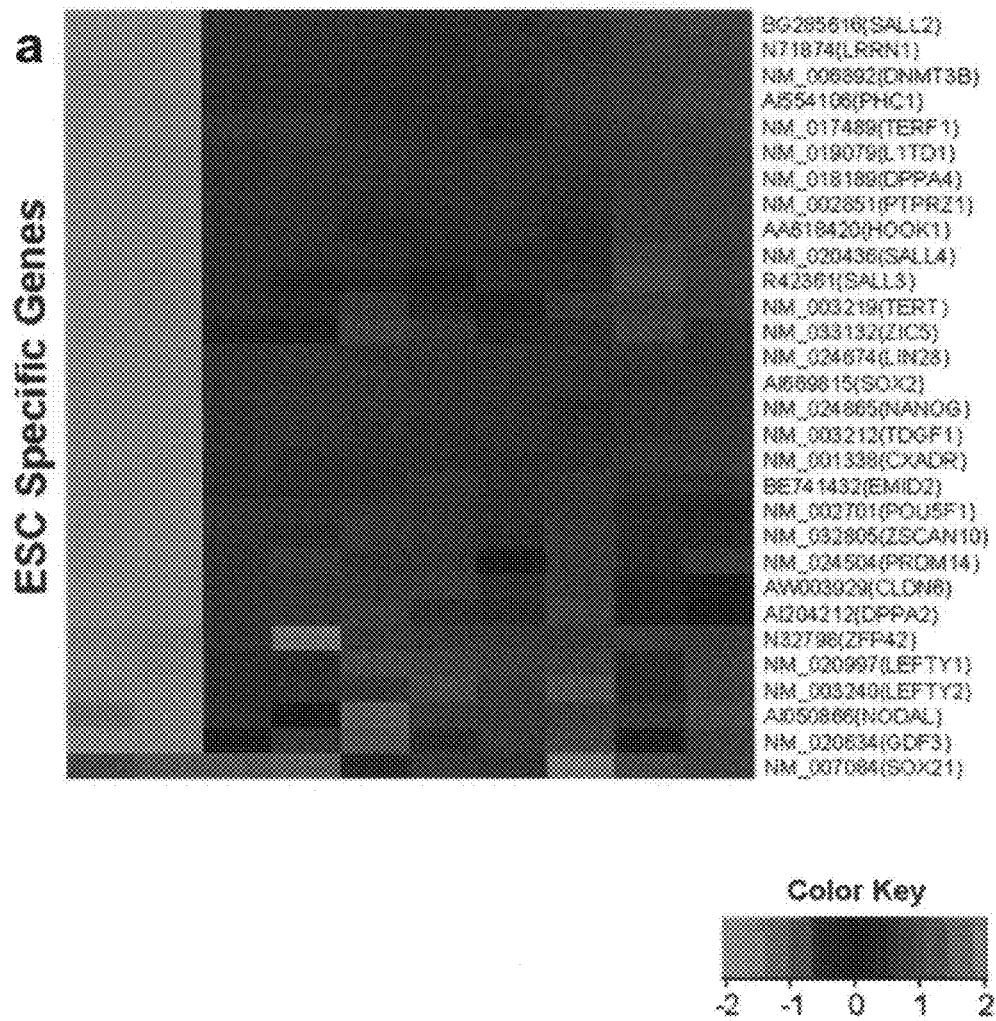
Figure 7B:
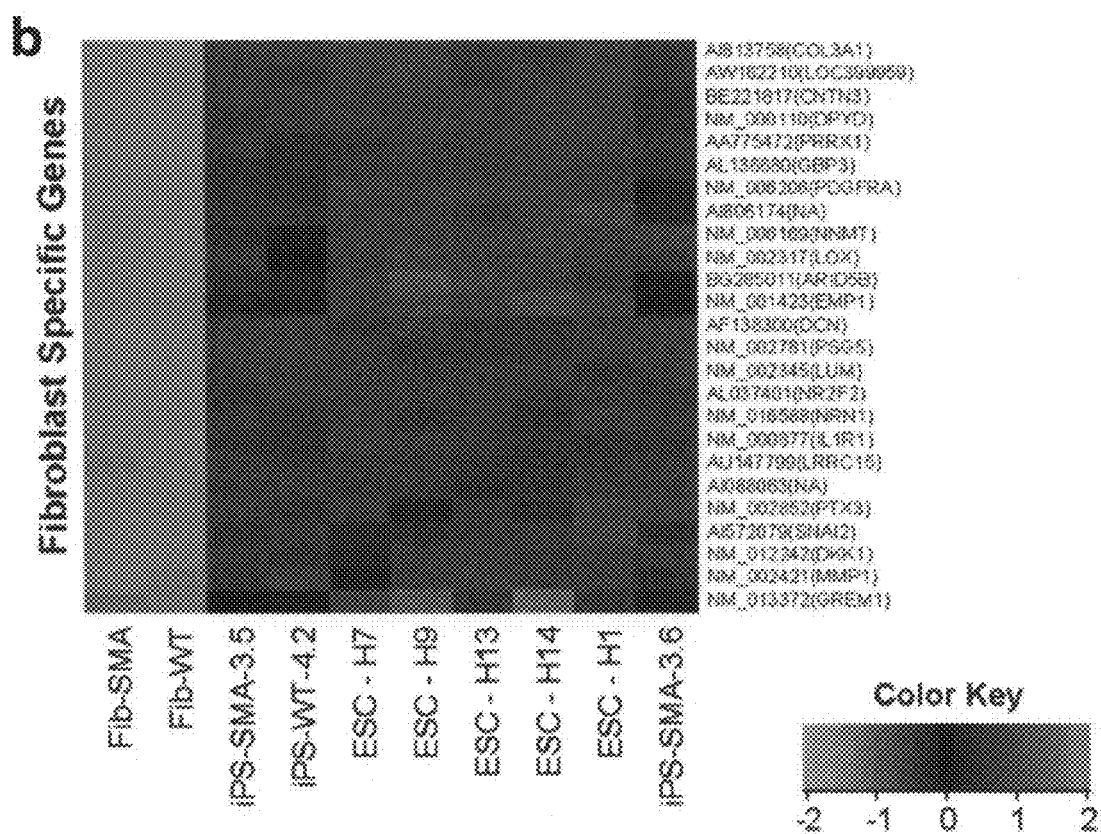

FIG. 7a, b. Heatmap analysis confirms differential gene expression among human ES cells, SMA fibroblasts, and WT fibroblasts. Reprogrammed iPS cells showed expression profiles similar to 30 well-known ES cell-enriched genes (top panel) and showed distinct differences from the top 25 fibroblast-enriched genes (bottom panel). Green=low expression; red=high expression.

Figure 8A:
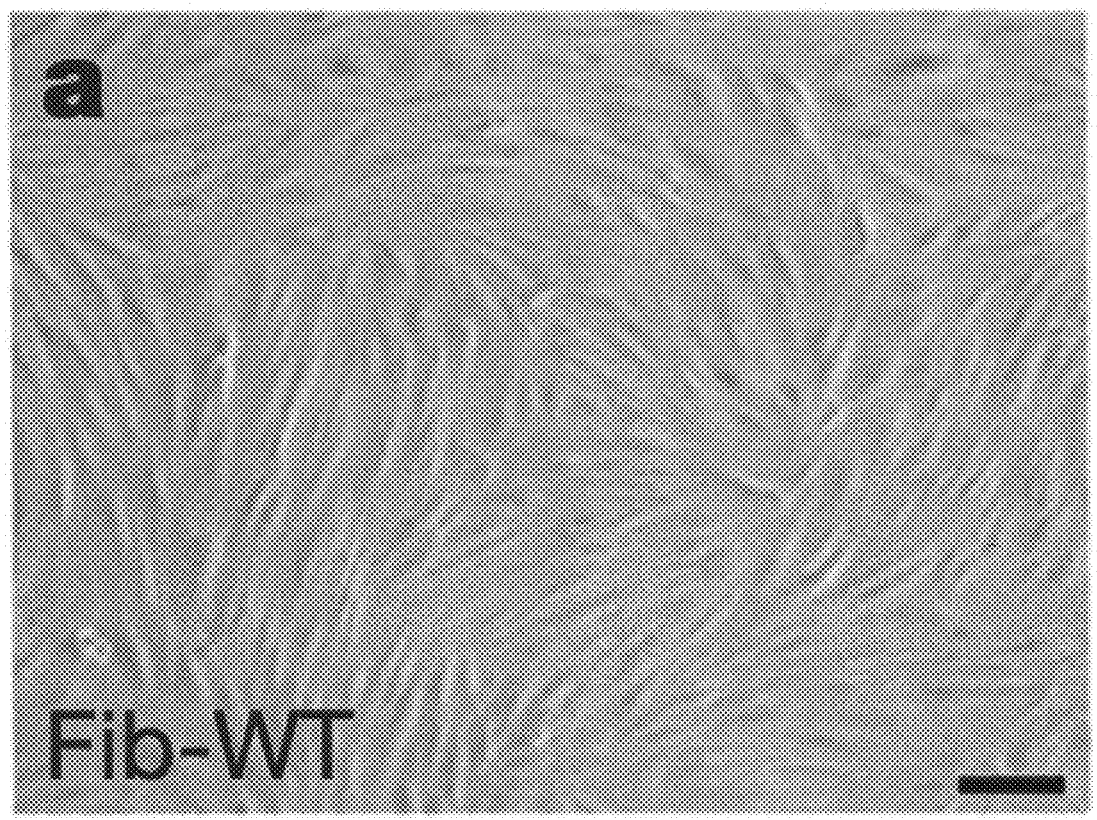
Figure 8B:
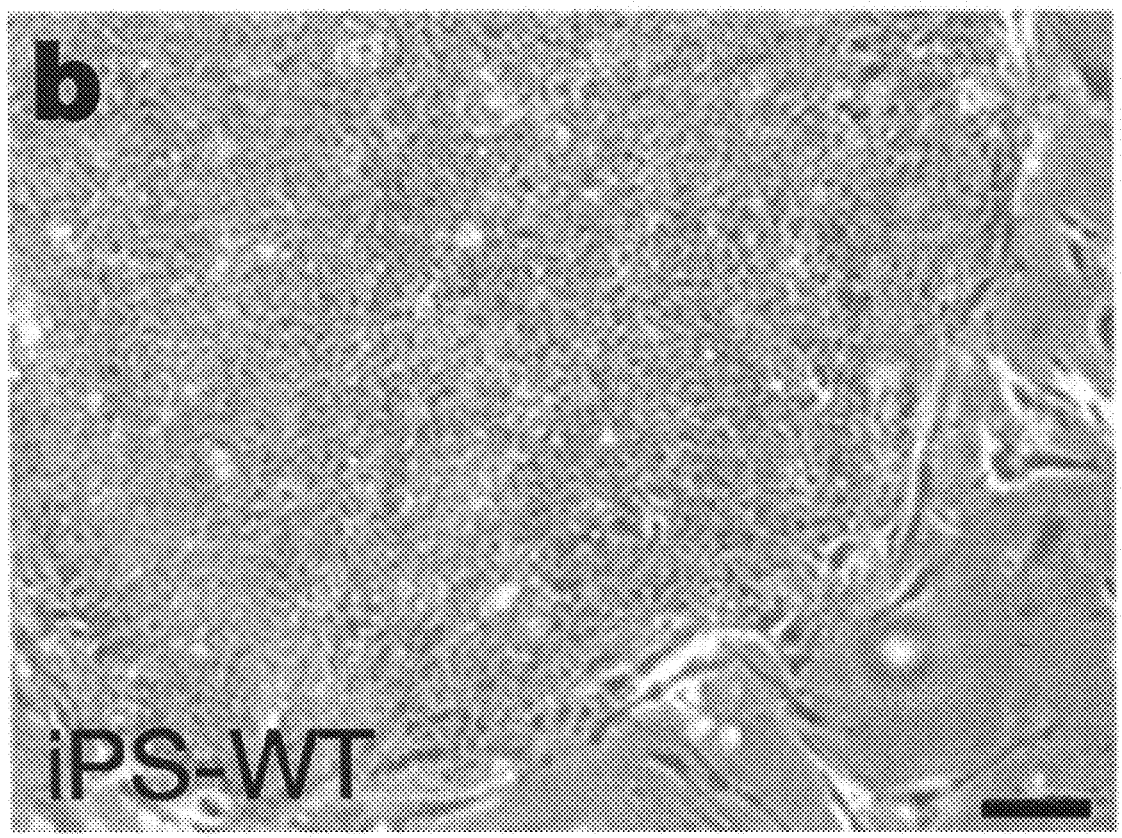
Figure 8C:
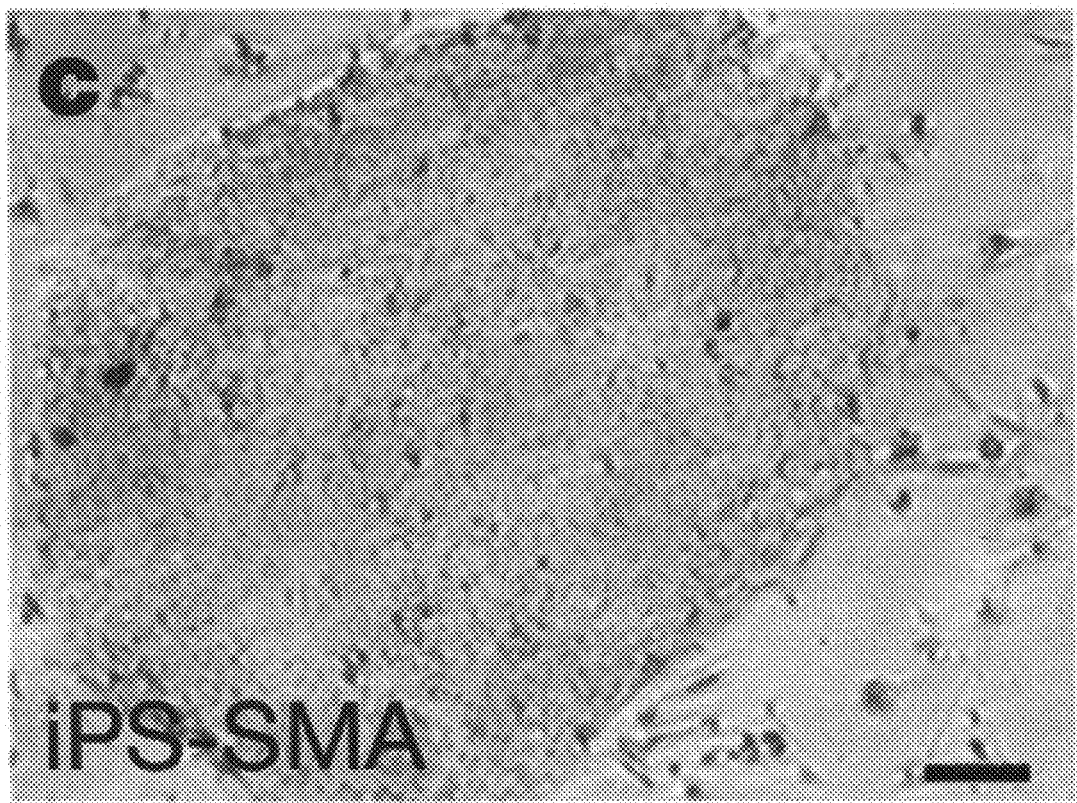
Figure 8D:
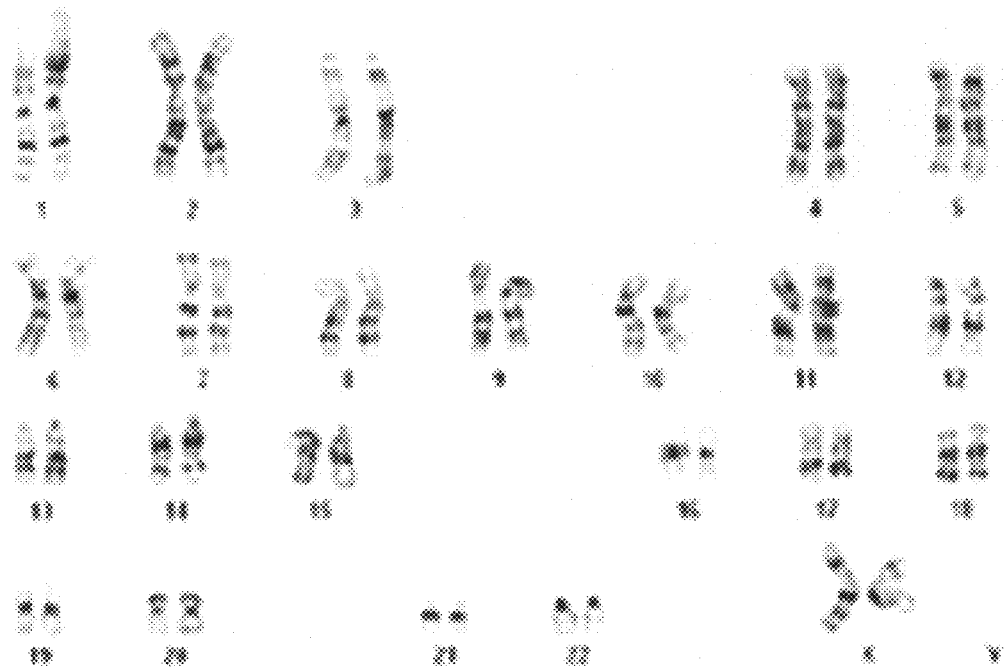
Figure 8E:
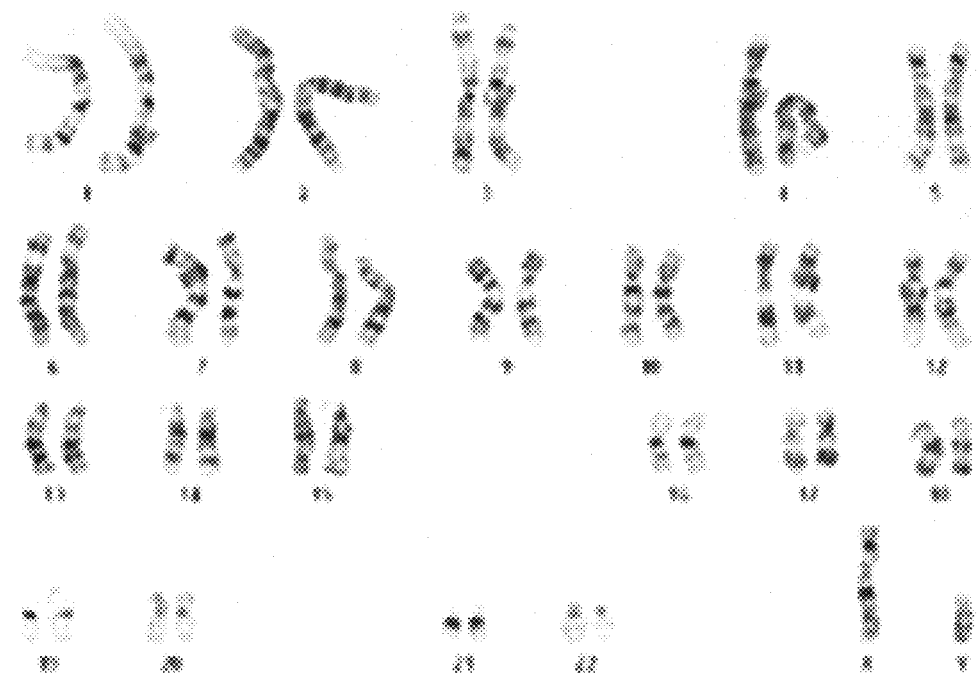
Figure 11G:
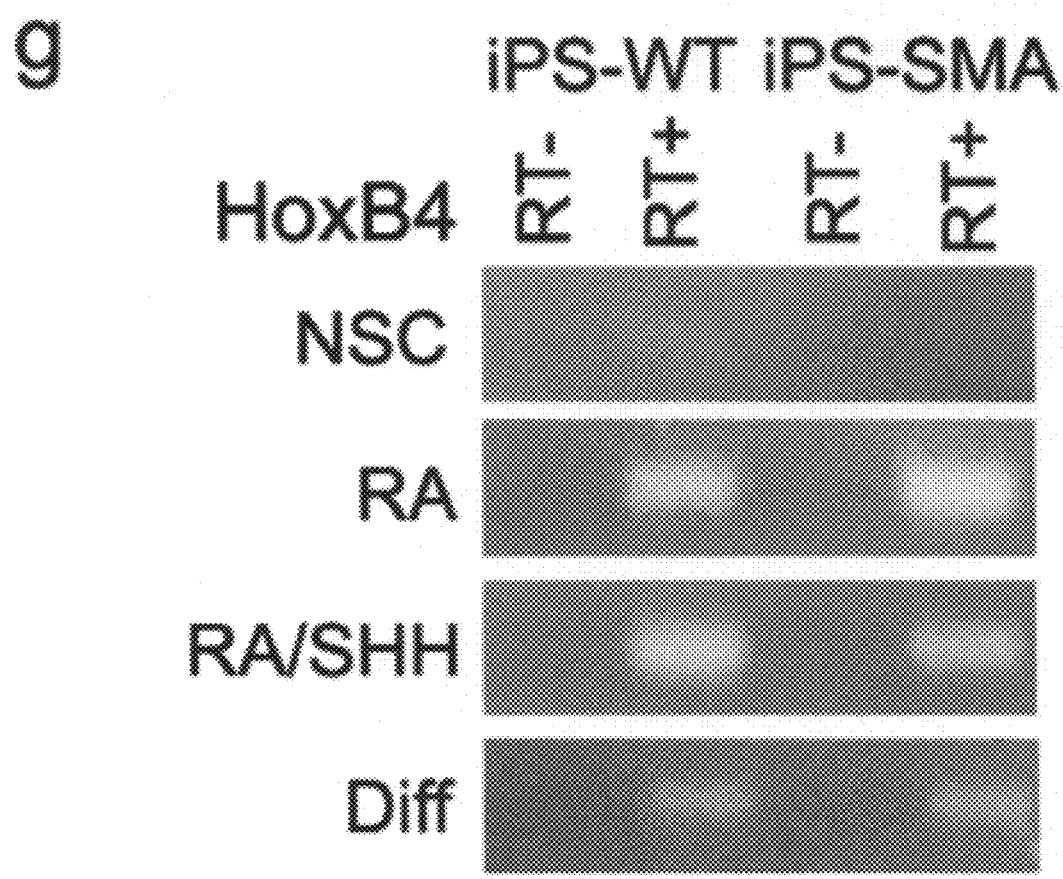

FIG. 8A-E. Newly generated iPS cells. FIG. 8A-C, iPS-WT and iPS-SMA cells formed tightly packed colonies in contrast to the spindle morphology of fibroblasts. FIG. 8D, E, No karyotypic abnormalities were observed.

FIG. 9A-B. iPS-SMA cells show decreased SMN transcripts. FIG. 9A: iPS-WT and iPS-SMA cells had levels of full-length (FL) and truncated, exon 7 deleted ($\Delta$7) SMN transcripts similar to their respective fibroblast lines (Fib-WT and Fib-SMA, respectively). FIG. 9B, Additionally, both Fib-SMA and iPS-SMA cells showed a specific lack of SMN1, although SMN2 full-length and $\Delta$7 transcripts were still present in all samples.

FIG. 10A-J. iPS-WT and iPS-SMA cells can generate cells in the neural lineage. FIG. 10A, B, iPS-WT and iPS-SMA cells generated nestin-positive neural progenitor cells (green). FIG. 10C, D, Tuj1-positive neurons (green) and GFAP-positive astrocytes (red) are shown. FIG. 10E-H, At 4-6 weeks of differentiation, HB9 (green) and ChAT (red) double-positive motor neurons (FIG. 10E, F), and SMI-32-positive (red) motor neurons (FIG. 10G, H) are shown, with magnified images shown in insets FIG. 10E, G, I. At 8 weeks, punctate synapsin (green) staining on SMI-32-positive motor neurons (red) was identified on iPS-WT cells (arrows). FIG. 10J, However, only diffuse synapsin (green) staining was observed on SMI-32-positive motor neurons (red) in iPS-SMA cells (arrows). Arrowheads in FIG. 10I and FIG. 10J denote punctate synapsin staining on SMI-32-negative cells. Nuclei are labeled with Hoechst nuclear dye (blue). Scale bar, 50 mm (FIGS. 10A-H) and 25 mm (FIG. 10I, J).

FIG. 11A-G. iPS-WT and iPS-SMA cells exhibit markers of motor neurons following lineage restriction. 11a,b, Olig2 (green); 11c,d, Islet 1 (green); and 11e,f, HB9 (green) positive cells were observed in both cell lines. Lineage restriction also induced HoxB4 expression as determined by PCR (11g). NCS (neural stem cell maintenance medium), RA (neural induction medium+retinoic acid), RA/SHH (RA medium plus sonic hedgehog), Diff (RA/SHH medium plus cAMP, ascorbic acid, GDNF, and BDNF). Scale bar=50 µm.

Figure 12:
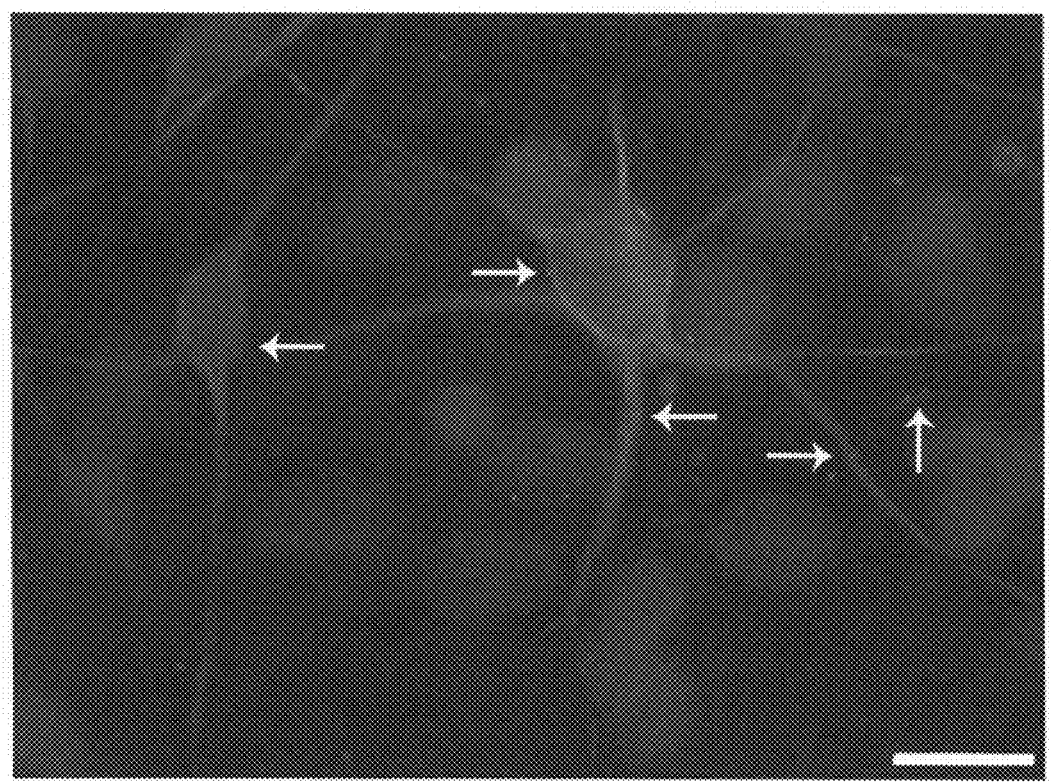

FIG. 12. High maintenance of synapsin staining shows pre-synaptic structures in iPS-WT derived motor neurons. At 8 weeks of differentiation, punctuate synasin staining is identified on the dendrites and cell bodies of SMI-32 positive motor neurons in iPS-WT cells. Scale bar=50 µm.

Figure 13I:
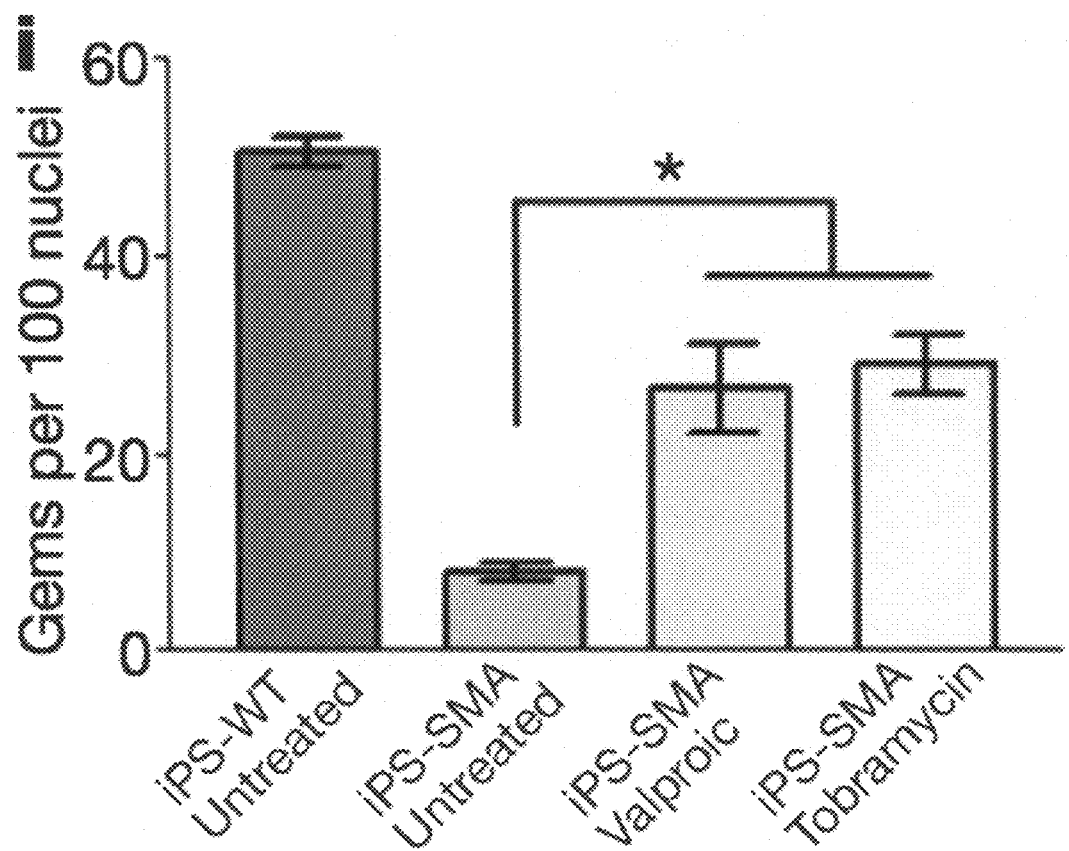
Figure 13J:
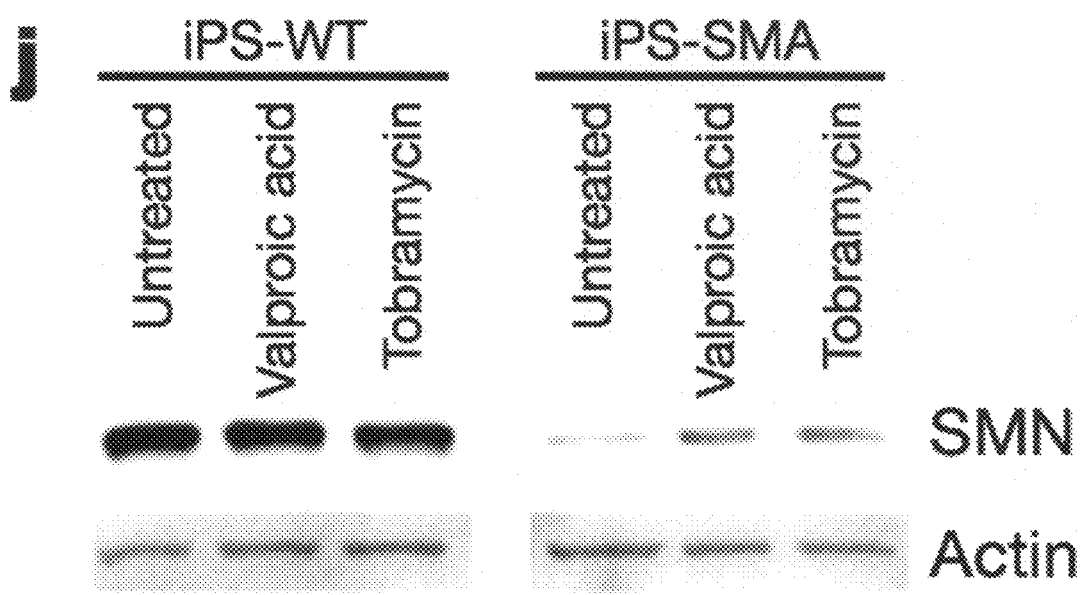
Figure 13K:
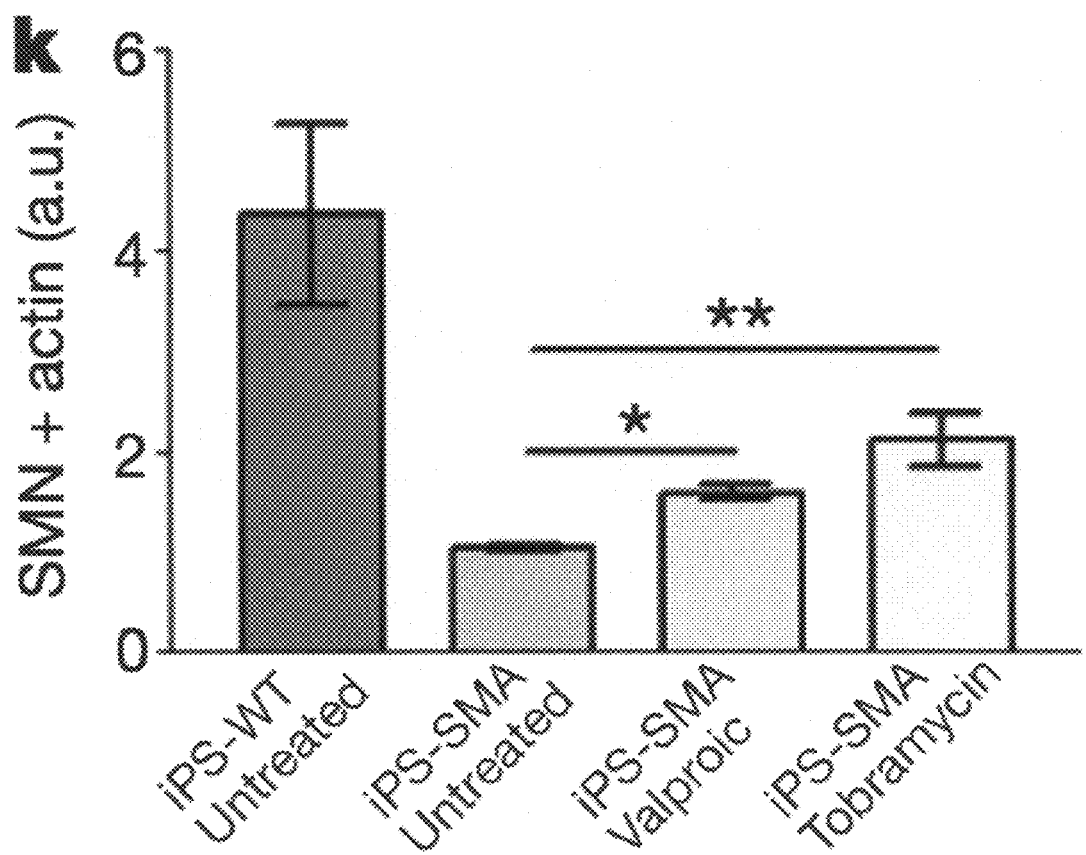

FIG. 13A-K. iPS-WT and iPS-SMA cells increase SMN protein in response to drug treatment. FIG. 13A-D, Untreated Fib-WT and iPS-WT cells show nuclear gem localization (FIG. 13A, C; gems indicated by arrows), whereas untreated Fib-SMA and iPS-SMA lack nuclear gems (FIG. 13B, D). FIG. 13E-I, After valproic acid (FIG. 13E, F) or tobramycin (FIG. 13G, H) treatment, iPS-SMA cells show a significant increase in the number of gems (P<0.05, ANOVA, FIG. 13I). FIG. 13J, K, Western blot analysis showed a significant 2-3-fold increase in SMN protein in valproic acid or tobramycin treated iPS-SMA cells compared to untreated iPS-SMA cells (n=3,*P<0.05, **P<0.01, ANOVA). a.u., arbitrary units. Data are presented as mean+/−s.e.m. Scale bar=50 mm.

FIG. 14. SMN protein can be identified in ChAT positive neurons. Following differentiation, nuclear gems can be detected in motor neurons of iPS-WT cells (arrows) using SMN and ChAT staining. Nuclei are labeled with DAPI. Scale bar=25 µm.

DESCRIPTION OF THE INVENTION

Generation of SMA Patient-Derived iPS Cells

In one embodiment, the present invention is a population of SMA patient-derived iPS cells derived from somatic cells, preferably primary fibroblasts, from an SMA patient, preferably a child with type 1 SMA. Typically, these iPS cells are capable of robust expansion in culture, maintaining the disease genotype, and differentiation into motor neurons that show selective deficits when compared to control cells, such as cells derived from the child's unaffected mother.

By "robust expansion," we mean that the cells are capable of the same indefinite number of passages and time in culture as typical iPS cells.

By "maintaining disease phenotype," we mean that every time the cells are differentiated, they show the loss of motor neurons over time as disclosed in the Examples. The cells also lack a functional SMN 1 gene.

By "differentiation into motor neurons," we mean the cells can differentiate into cells with the markers, cell function and cell morphology typical of motor neurons.

In one embodiment, the present invention is a method of producing SMA-patient-derived iPS cells comprising the steps of obtaining fibroblasts, or other somatic cells, from an SMA patient and inducing iPS cell formation from the somatic cells. Many other starting cells have been used to create iPS cells. Tissue specific stem cells may give higher frequencies than more differentiated cells like fibroblasts. For example, Daley et al. have used a hematopoietic stem cell population defined by CD34+ as a starting population (see Loh et al., Generation of induced pluripotent stem cells from human blood, Blood, 113, 5476-5479, 2009). Others have shown successful derivation of iPS Cells from cord blood, placental stem cells, keratinocytes, spermatogonial stem cells and others.

One would first obtain somatic cells, preferably fibroblasts, from an SMA patient. Patients who are suspected of SMA will typically have a confirmatory genetic test. This test will show complete deletion of the SMN 1 gene and confirm the diagnosis. The severity of the disease then depends on the copy number of SMN2, as described earlier. Copy number is not normally tested by doctors because the assay is not reliable. Often, there is a period of observation of the clinical symptoms in order to confirm diagnosis.

Reprogramming of patient cells to iPS cells may be achieved after infection with lentiviral constructs encoding OCT4, SOX2, NANOG and LIN28 (as disclosed in the Examples), but other methods for reprogramming somatic cells to iPS cells, many of which are known in the art, could also be utilized to generate SMA-iPS cells of the present invention. For example, one could use the methods of Yamanaka or Daley (see Takahashi et al. Induction of pluripotent stem cells from adult human fibroblasts by defined factors, Cell, 131, 861-872, 2007; Park et al., Reprogramming of human somatic cells to pluripotency with defined factors, Nature, 451, 141-146, 2008). One could also utilize small molecules for reprogramming or piggyBac transposition methods (see Guo et al., Klf4 reverts developmentally programmed restriction of ground state pluripotency, Development, 136, 1063-1069, 2009; Kaji et al. Virus-free induction of pluripotency and subsequent excision of reprogramming factors, Nature, 458, 771-775, 2009; Shi et al., Induction of pluripotent stem cells from mouse embryonic fibroblasts by oct4 and klf4 with small-molecule compounds. Cell Stem Cell 3, 568-574, 2008; Shi et al., A combined chemical and genetic approach for the generation of induced pluripotent stem cells. *Cell Stem Cell* 2, 525-528, 2008; Woltjen et al., piggyBac transposition reprograms fibroblasts to induced pluripotent stem cells, Nature, 458, 766-770, 2009; Zhou, H. et al. Generation of Induced Pluripotent Stem Cells Using Recombinant Proteins, Cell Stem Cell, 4, 381-384).

To confirm that reprogramming of wild-type and SMA fibroblasts to a pluripotent state has occurred, one may wish to use standard techniques including, but not limited to, quantitative PCR with reverse transcription (qRT-PCR), teratoma formation, DNA fingerprinting and microarray analysis. A recent paper from Daley discloses pluripotency criteria (see Chan et al., Live cell imaging distinguishes bona fide human iPS cells from partially reprogrammed cells, Nat. Biotech., 27, 1033-1037, 2009). Typically, one would look for teratoma formation and expression of endogenous Oct4, SSEA, TRA and other markers. One would also look for the ability to make embryoid bodies that produce all three dermal lineages.

Figure 1:
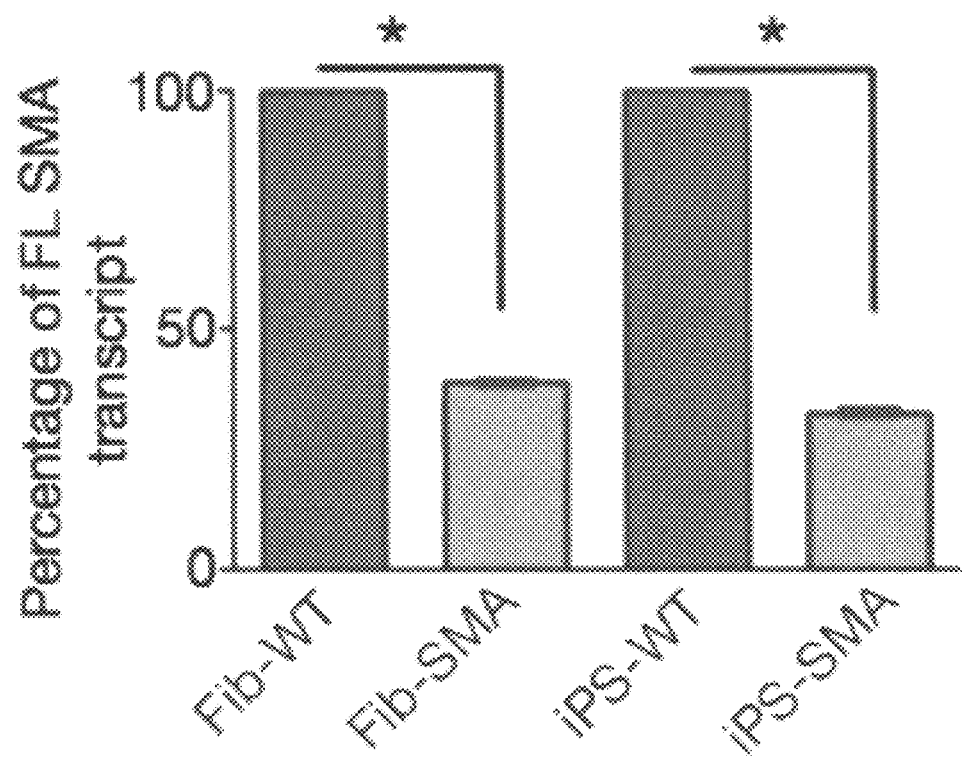
FIG. 1, iPS-SMA cells show decreased SMN transcripts. qRT-PCR showed reduced full-length SMN transcript in both fibroblasts (61.1%+/−0.6 reduced) and iPS cells (67.4%+/−

To confirm whether the derivation of iPS cells affects SMN production, RT-PCR can be used to compare SMN levels to the wild-type fibroblasts (Fib-WT); iPS-SMA cells should have lower levels similar (±10%) to the fibroblast-SMA cells. The Examples below disclose a typical SMA-patient-derived iPS population wherein a significantly reduced level of full-length SMN transcripts was found. FIG. 1 indicates a 61-67% reduction compared to wild type cells. We envision that this reduction will be at least 70% compared to wild-type cells and could be much less than the cells disclosed in the Example, which were taken from an SMA1 patient, if the patient from whom the cells are derived has a more severe form of SMA. As expected, owing to the maintenance of SMN2 function in this disorder, transcripts for some full-length SMN and the alternatively spliced product lacking exon 7 (D7) should be present. Techniques known to the skilled artisan, including but not limited to qRT-PCR, can be used to confirm that SMA iPS cells of the present invention have reduced levels of full-length SMN transcripts compared to WT cells.

The Examples below disclose data that demonstrate that the generation of iPS cells does not alter the critical gene expression profiles or alternative splicing events of SMN1 and SMN2 in disease-specific contexts.

An overall preferred process is illustrated in FIG. 2. Primary fibroblasts are taken from a patient with SMA. Following lentiviral transduction of the pluripotency genes, iPS cells are generated from the SMA fibroblasts. These SMA-iPS cells may be expanded and pushed toward the neural lineage. Motor neurons derived from SMA-iPS cells undergo continual degeneration over time. Unlike previous reports of iPS cells generated from fibroblasts of patients with various diseases, these SMA-iPS cells retain the SMA disease phenotype and have the capacity for differentiation into neuronal cells that exhibit a phenotype typical of SMA.

Neuronal Differentiation of SMA Patient-Derived iPS Cells

Given that the SMA phenotype is evident in patient neuronal cells, an important feature of the SMA patient-derived iPS cells of the present invention is their capacity for neuronal differentiation. To establish whether the lack of SMN1 affects neuronal differentiation or survival in this model system, the Examples below demonstrate that neurons and astrocytes were generated from both iPS-SMA and iPS-WT cells.

In one embodiment, the present invention is a population of neural cells, preferably motor neurons, derived from the SMA-patient-derived iPS cells described above. Traditional techniques known to skilled artisans including, but not limited to, embryoid body formation (see Thomson et al., Embryonic stem cell lines derived from human blastocysts, Science, 282, 1145-1147, 1998) can be utilized for neuron and astrocyte differentiation. We found embryoid body formation to be inefficient, so an alternate protocol was developed.

Briefly, iPS cultures are removed from their feeder layers and grown as floating iPS spheres in a defined media (defined below in the Examples) for a minimum of two weeks. These spheres could be continually passaged using a chopping method (Ciccolini & Svendsen, FGF-2 promoted acquisition of EGF responsiveness in mouse striatal precursor cells: Identification of neuronal precursor cells responding to both EGF and FGF-2, J. Neurosci. Res., 18, 7869-7880, 1998) that avoids losing cell-cell contact. Spheres are then dissociated and plated onto laminin-coated coverslips. The iPS-SMA and iPS-WT spheres will generate nestin-positive cells indicative of a neural stem cell phenotype. These iPS spheres are then grown in a neural induction medium (defined below) containing retinoic acid for one week, followed by a further week of retinoic acid and sonic hedgehog (SHH).

Spheres are then seeded onto laminin-coated coverslips for another 2-6 weeks and grown in the presence of neuronal differentiation factors known in the art, such as sonic hedgehog, GDNF and other growth factors. One week after plating, long fine processes resembling neuronal axons are observed and neural-like cells will migrate out from the sphere. Both iPS-SMA and iPS-WT spheres generate cells that express known motor neuron transcription factors during the differentiation process. Typical transcription factors include HB9 and islet 1. Immunostaining will identify positive neurons in all cultures after four weeks of differentiation, but at this point there is no significant difference between the iPS-SMA and iPS-WT cultures in the number of motor neurons or their size, indicating that iPS-SMA cells are indeed capable of generating motor neurons. The Examples disclose no significant difference between the iPS-SMA and iPS-WT cultures in the number of motor neurons (12.6%+/−2.2 and 9.5%+/−2.4, respectively) or their size (641.0 mm$^2$+/−81.3 and 669.8 mm$^2$+/−59.1, respectively, FIG. 3A, B).

When cultured for another two weeks the iPS-SMA cultures had significantly fewer motor neurons with a reduced size compared to the iPS-WT cultures. The Examples disclose significantly fewer motor neurons (4.3%+/−2.0) with a reduced size (383.1 mm$^2$+/−38.6) compared to the iPS-WT cultures (24.2%+/−4.0, 654.8 mm$^2$+/−32.6, FIG. 3A, B). However, there is no significant difference in the number of total Tuj1-positive neurons in either iPS-WT or iPS-SMA cells at six weeks of differentiation, suggesting that there is a specific effect of the SMA phenotype on motor neurons. (TuJ1 labels all neurons in the culture showing that the effect of SMN1 deletion was specific to the motor neurons only.) The Examples disclose data that show that iPS-SMA cells can produce similar numbers of neurons and motor neurons initially, but that the disease phenotype selectively hinders motor neuron production and/or increases motor neuron degeneration at later time points.

Note that the examples show that the cultures can be differentiated to a motor neuron phenotype but that there are also other types of neurons in the population that could be purified. At least 20% or more of the cells are motor neurons.

In a successful embodiment of the invention, one would expect that a population of motor neurons derived from SMA patient iPS cells would have significantly fewer motor neurons with reduced size compared to iPS-WT cultures. One would expect fewer than approximately 5% of the resulting cells will be motor neurons compared to a wild-type culture of approximately 25%. Preferably, one would compare the culture after 6 weeks of differentiation.

In a preferred version of the present invention, the differentiated cell population is representative of the human spinal cord in that ~20% (+/−10%) of the cells are neurons and of these ~20-30% (+/−10%) are motor neurons.

Drug Screening Using hES Cells and Derivatives

In general, hESCs may be used for drug screening by isolating the cells from embryos derived from patients with the disease and studying the cells that over-express or under-express disease genes. The fundamental idea is to expand the cells, differentiate them into the desired cell type, and then screen for drugs that may correct an observed disease phenotype. Whole animal and cell based systems have been vital to the understanding of disease genetics and mechanisms, but hESCs may offer additional information. For example, hESCs allow for the study of human genes and down-stream targets that are either absent or differentially regulated in animal models. Furthermore, hESCs are not immortalized, so the cells provide a unique window into human development that traditional human cell lines cannot provide. Finally, the fully specialized cell types that can be generated from hESCs allow investigation of cell types that may not be readily available in other models. Using patient fibroblast samples, many attempts are currently underway to find compounds that can increase the production of the SMN2 protein. However, motor neurons are the cells most severely affected by the disease and have yet to be fully studied.

The present invention combines the advantages of hESC and somatic cells screening. The Examples below disclose that iPSCs generated from a child with SMA continue carrying the genetic deficit while being expanded to large numbers. These cells can also be differentiated into motor neurons that then undergo disease-specific cell death in the culture dish. This work represents a very powerful example of a model in which to explore both disease mechanisms and novel compounds that may block this disease-specific cell death pattern. Interestingly, drugs known to activate SMN protein in fibroblasts also worked in neural derivatives of iPSCs.

Therefore, in another embodiment, the invention is a test system. One may wish to screen for new drugs or confirm the activity of proposed SMA treatments. If one could determine whether currently proposed SMN-inducing compounds increase SMN levels in the iPS-SMA cellular context, this determination would be an important proof-of-principle for the further development of specific drugs.

One useful measure of SMN levels is the evaluation of "gem localization." SMN protein is found in both the cytoplasm and nuclear aggregate structures called gems, and the number of gems present is inversely correlated to disease severity (see Coovert et al., The survival motor neuron protein in spinal muscular atrophy. Hum. Mol. Genet., 6, 1205-1214, 1997; Lorson et al., SMN oligomerization defect correlates with spinal muscular atrophy severity, Nat. Gen. 19, 63-66, 1998; Wehner et al., Survival motor neuron protein in the nucleolus of mammalian neurons, Brain Res. 945,160-173, 2002; Lorson et al., Identification and characterization of the porcine (Sus scrofa) survival motor neuron (SMN1) gene: an animal model for therapeutic studies, Dev. Dyn., 237, 2268-2278, 2008). The Examples below assessed nuclear gem localization in iPS-SMA- and iPS-WT-derived neurons and astrocytes in the presence or absence of valproic acid or tobramycin, two compounds shown to increase SMN protein levels. After two days of drug treatment, there was no significant increase in gem localization in treated compared to untreated iPS-WT cells. However, valproic acid and tobramycin significantly increased the number of gems in treated compared to untreated iPS-SMA cells. This suggests that iPS-SMA cells of the present invention respond to drug treatment in a similar fashion to fibroblast-SMA cells and are useful for new drug screening specifically on motor neurons in future studies.

Compounds could be tested at multiple stages of the growth and differentiation of the iPS-SMA cells (i.e. at the colony stage, as neural progenitor cells [nestin positive], as neurons/astrocytes, or as motor neurons) and at different concentrations and times to determine a dose response. The advantage of testing motor neurons would be that these cells would have the best chance of having similar receptors and functions as in vivo motor neurons to give the best prediction of how a compound will affect the cell type primarily affected by the disease. However, it's possible that in a developmental disease such as SMA, treating prior to full motor neuron differentiation (e.g. in the neural progenitor stage) may help the survival of the motor neurons yet to develop so one may wish to test cells at all stages of development.

Gem counts are a direct indication of the effect of the drug on SMN protein production. Examination of gem count will probably be a standard outcome. One could also look at total motor neuron survival (in terms of neuron number and reduction in markers of cell death) as well as functional outcomes (e.g. electrophysiology). See Bromberg, et al., *Muscle and Nerve* 25:445-447, 2002.

SMA fibroblasts have ~5 gems/100 nuclei, with most cells having 0-1 gems/cell. WT fibroblasts have ~100-150 gems/100 nuclei with many of them having 3-5+ gems/cell. In some drug screens using the SMA fibroblasts, successful compounds increase the total number of gems and the number of gems within each cell. An example of this is Maths et al., *Hum Genet* 120:589-601, 2006.

Some of the novel compounds that have been tested are part of drug classes called aminoglycosides or histone deacetylases inhibitors because these compound classes play roles in transcription or translation of the genome. The SMN2 gene doesn't get translated properly because of a nucleotide transition; some of these compounds then target this area to alter the "reading" of the SMN2 gene and encourage it to produce more functional protein. Many compounds to be tested would be dealing with altering the SMN2 function because SMA patients lack SMN1. Alternatively, compounds that promote cell survival (e.g. compounds that stimulate intracellular protective pathways or promote secretion of growth factors) would be useful independent of SMN2 function.

Utilization of the SMA patient-derived iPS cells of the present invention, and derivatives of these cells, for drug screening is an embodiment of the present invention. Basically, one would expose SMA-patient-derived iPS cells or cells derived from these iPS cells, such as motor neuron cells, to a test compound and monitor SMN levels. SMN function could be monitored by directly looking at protein production, gem localization, or SMN RNA function (e.g. read-through of the Δ7 transcripts to allow full-length SMN protein to be produced). Levels comparable to control SMA-patient-derived iPS cells that have not been exposed to the test compound (+/−10%) would indicate that the compound is ineffective.

In the disease, motor neurons are selectively affected. An increase of SMN production (preferably at least 20%) would indicate a compound useful for further screening. If drugs are screened on fibroblasts, the drug may increase SMN levels through a mechanism that does not exist in motor neurons. (For example, motor neurons may not express the receptor that the fibroblast has so cannot respond to the drug.)

In another embodiment, one would examine the differentiation of SMA patient-derived iPS cells into motor neurons in the presence of a test compound and determine whether a decrease, relative to cells without the test compound, in motor neuron degeneration takes place. One would typically expect to see a level of degeneration within 10% of the level of wild type cells to indicate a successful compound.

In another embodiment, one would examine the effect of the test compound on neural cell survival. Compounds that increase neural cell survival, relative to identical SMA-patient derived motor neurons that have not been exposed to the test compound, would be an excellent candidate for further drug testing.

EXAMPLES

Methods iPS cell culture and lentiviral infection. iPS cells were maintained on irradiated mouse embryonic fibroblasts as previously described (Yu, J. et al. Induced pluripotent stem cell lines derived from human somatic cells, Science 318, 1917-1920, 2007). Fibroblast cells (GM03813 and GM03814, Coriell Inst.) were cultured in Minimum Essential Medium (Eagle) (Invitrogen) supplemented with 10% heat-inactivated fetal bovine serum (HyClone Laboratories). Lentiviral transduction of fibroblast cells was performed as previously described (Yu, J. et al. Induced pluripotent stem cell lines derived from human somatic cells, Science 318, 1917-1920, 2007).

Neural differentiation. iPS spheres were generated by lifting intact iPS colonies from the feeder layers after collagenase treatment (1 mg, Gibco) and placing them directly into a human neural progenitor growth medium (Stemline, Sigma) supplemented with 2% B27 (Gibco), 100 ng basic fibroblast growth factor (bFGF, Chemicon), 100 ng epidermal growth factor (EGF, Chemicon), and 5 mg heparin (Sigma) in polyhema-coated flasks to prevent attachment and were passaged weekly using a chopping technique (Svendsen, C. N. et al. A new method for the rapid and long term growth of human neural precursor cells, J. Neurosci. Methods 85, 141-152, 1998). To induce neuron and astrocyte differentiation, spheres were dissociated with accutase (Chemicon) and plated onto polyornithine/laminin (Sigma)-coated coverslips in Stemline/2% B27 without bFGF, EGF and heparin for 1 week. To induce motor neuron differentiation, spheres were placed in neural induction medium (1:1 DMEM/F12 and 1% N2 supplement (Gibco)) in the presence of retinoic acid (0.1 mM) for 1 week followed by the addition of sonic hedgehog (SHH, 100 ng, R&D) for another week. Spheres were then plated onto polyornithine/laminin-coated coverslips in retinoic acid and SHH medium supplemented with cAMP (1 mM), ascorbic acid (200 ng), brain-derived neurotrophic factor and glial cell line-derived neurotrophic factor (both 10 ng, PeproTech Inc.) for a further 2-6 weeks.

RNA isolation and PCR analysis. Total RNA was isolated using the RNeasy Mini Kit (Qiagen) with on-column DNase I digestion or Tri reagent (Sigma). Complementary DNA was generated from 1-4 mg total RNA using SuperScript III (Invitrogen). RT-PCR and/or qRT-PCR were performed using specific primer sequences (Table 1). Full-length and Δ7 SMN products were gel purified and digested with Dde1 specifically cleaving SMN2, giving expected band sizes of 713 nucleotides (undigested full-length), 436 and 277 nucleotides (SMN2 full-length), and 382 and 277 nucleotides (SMN2 Δ7).

TABLE 1

Specific gene primers used for PCR analysis. CDR indicates the primers span the coding region of the gene allowing for total gene expression whereas 3UTR indicates the primers span the 3'untranslated region of the gene. F and R indicate the forward and reverse primers, respectively.

| Genes | Primer Direction | Sequences (5' to 3') | SEQ ID NO. |
|---|---|---|---|
| GAPDH | | | |
| CDR | F | gtggacctga cctgccgtct | 1 |
| | R | ggaggagtgg gtgtcgctgt | 2 |
| OCT4 | | | |
| CDR | F | cagtgcccga aacccacac | 3 |
| | R | ggagacccag cagcctcaaa | 4 |
| 3UTR | F | agtttgtgcc agggttttg | 5 |
| | R | acttcacctt ccctccaacc | 6 |
| NANOG | | | |
| 3UTR | F | tttggaagct gctggggaag | 7 |
| | R | gatgggagga ggggagagga | 8 |
| CDR | F | cagaaggcct cagcacctac | 9 |
| | R | attgttccag gtctggttgc | 10 |
| SOX2 | | | |
| CDR | F | tacctcttcc tcccactcca | 11 |
| | R | ggtagtgctg ggacatgtga | 12 |

TABLE 1-continued

Specific gene primers used for PCR analysis.
CDR indicates the primers span the coding
region of the gene allowing for total gene
expression whereas 3UTR indicates the primers
span the 3'untranslated region of the gene.
F and R indicate the forward and reverse
primers, respectively.

| Genes | Primer Direction | Sequences (5' to 3') | SEQ ID NO. |
|---|---|---|---|
| 3UTR | F | agtctccaag cgacgaaaaa | 13 |
| | R | tttcacgttt gcaactgtcc | 14 |
| LIN28 | | | |
| CDR | F | aagcgcagat caaaaggaga | 15 |
| | R | ctgatgctct ggcagaagtg | 16 |
| 3UTR | F | agtggcctgg atagggaagt | 17 |
| | R | cttggctcca tgaatctggt | 18 |
| SMN | FL-F | caaaaagaag gaaggtgctc acatt | 19 |
| | FL-R | gtgtcattta gtgctgtct atgc | 20 |
| | Δ7-F | catggtacat gagtggctat catactg | 21 |
| | Δ7-R | tggtgtcatt tagtgctgct ctatg | 22 |
| HOXB4 | F | gcaaagagcc cgtcgtctac | 23 |
| | R | cgtgtcaggt agcggttgta | 24 |

Karyotyping and DNA fingerprinting. Standard G-banding chromosome analysis was performed in the Cytogenetics Lab at WiCell Research Institute. To confirm the fibroblast origins of the iPS-SMA and iPS-WT cells, short tandem repeat (STR) analysis was performed by Cell Line Genetics.

Teratoma formation. Two 10-cm dishes of iPS-WT clone 4.2, iPS-SMA clone 3.5, and clone 3.6 (50% confluent) grown on irradiated mouse embryonic fibroblasts were injected into the hind limb muscle of two mice. All iPS clones gave rise to teratomas. Control mice injected with $8.5 \times 10^6$ Fib-WT and $11 \times 10^6$ Fib-SMA failed to form teratomas. Haematoxylin and eosin staining of teratoma sections was performed after 7-10 weeks.

Microarray analysis. Human genome U133 Plus 2.0 Gene-Chip arrays carrying 54,675 probe sets (Affymetrix) were used for microarray hybridizations to examine the global gene expression. Approximately 3 mg of RNA from each sample was labeled using the MessageAmp Biotin II-Enhanced IVT kit (Ambion) following manufacturer's instructions. All arrays were hybridized at 45° C. for 16 h and scanned using an AFX GC3000 G7 scanner.

The gene expression raw data were extracted using the AFX Expression Console software. Quality control was done on the basis of Affymetrix quality control metrics. The qualified data sets were then analyzed in the R statistical environment, freely available under the GNU General Public License using bioconductor libraries. All chips were normalized by the quantile method (Bolstad et al., Bioinformatics 19, 185-193, 2003) and background corrected using robust multi-array analysis (RMA) followed by summarization using median polish (Irizarry, R. A. et al. Exploration, normalization, and summaries of high density oligonucleotide array probe level data, Biostatistics 4, 249-264, 2003) to get the probe set level measurement. A total of 54,675 probe sets was collapsed to 51,337 transcripts by taking the average log intensity values for probe sets representing common accession numbers. Hierarchical cluster analyses were carried out with 1-PCC (Pearson correlation coefficient) as the distance measurement. The maximum distance between cluster members was used as the basis to merge lower-level clusters (complete linkage) into higher-level clusters. Multiscale bootstrap resampling (10,000 bootstraps) was applied to the hierarchical clustering, P values of hypotheses were calculated, and bootstrap probabilities were determined for each cluster (Suzuki, R. & Shimodaira, H. Pvclust: an R package for assessing the uncertainty in hierarchical clustering, Bioinformatics 22, 1540-1542, 2006).

HeatMap generation and data visualization. For each gene, the average expression level was calculated across five normal human embryonic stem cell lines and the two SMA or wild-type fibroblast cell lines. The fold changes were calculated for all the genes in the SMA and wild-type fibroblast cell lines over the corresponding average in human embryonic stem cells. The top 25 genes most specifically expressed in SMA and wild-type fibroblasts and 30 genes that are known to be enriched in human embryonic stem cells were selected for the HeatMap generation. The log intensities of these 55 genes were standardized so that their expression values across all samples have mean 0 and standard deviation 1. The standardized values were reordered and displayed in a heat map, with the spectrum ranging from green (low level) to red (high level).

Immunocytochemistry. Cells were fixed in 4% paraformaldehyde or 1:1 acetone/methanol for 20 min at room temperature and rinsed with PBS. Nonspecific labeling was blocked and the cells were permeabilized with 5% normal goat serum and/or 5% normal donkey serum containing 0.2% Triton X-100 in PBS for 30 min at room temperature. Cells were rinsed with PBS and then incubated with primary antibodies for 1 h at room temperature or overnight at 4° C. Cells were then labeled with the appropriate fluorescently tagged secondary antibodies. Hoechst nuclear dye was used to label nuclei. Gems were counted in 100 nuclei, and positively stained neurons were counted and measured on five areas on each of three coverslips using Metamorph software. All data were analyzed using Prizm statistical software.

Protein isolation and western blot analysis. Cells were isolated, suspended in 1% Triton X-100 lysis buffer supplemented with 1% protease inhibitor cocktail (Sigma), triturated and centrifuged at 16,060 g for 10 min at 4° C. Ten to twenty micrograms of protein was separated on 12% SDS-polyacrylamide gel, transferred to a nitrocellulose membrane and probed with a primary antibody against SMN (mouse monoclonal), followed by a horseradish-peroxidase-conjugated secondary antibody (Promega), and then visualized using ECL chemiluminescence (Amersham). As a control, the membrane was stripped and re-probed for beta-actin. For semiquantitative analysis, SMN signal intensity was analyzed and corrected with respect to beta-actin.

Results and Discussion

Characterization of iPS Cells

We generated iPS cells from primary fibroblasts from a type 1 SMA patient and his unaffected mother after infection with lentiviral constructs encoding OCT4 (also known as POU5F1), SOX2, NANOG and LIN28 (Yu, J. et al. Induced pluripotent stem cell lines derived from human somatic cells, Science 318, 1917-1920, 2007) (FIG. 2). Two SMA clones (3.5 and 3.6) and one wild-type clone (4.2) propagated robustly when maintained on mouse embryonic fibroblasts. Quantitative PCR with reverse transcription (qRT-PCR), teratoma formation, DNA fingerprinting and microarray analysis all indicated that reprogramming of wild-type and SMA fibroblasts to a pluripotent state occurred, along with repression of the exogenously introduced genes (FIG. 4A-E, Tables 2-3 and FIGS. 5-7). Only the 3.6 clone (iPS-SMA) and the 4.2 clone (iPS-WT; FIG. 8A-C) were used for further evaluation in this study. Both the iPS-SMA and iPS-WT cells grew at similar rates and maintained a normal karyotype for at least 12 weeks (FIG. 8D, E).

TABLE 2 iPS clones were efficiently reprogrammed. Correlation coefficient analysis shows significant correlation of reprogrammed iPS cells to the other reprogrammed clones and to five different hESC lines (0.98-0.99) rather than to the original fibroblast lines (0.86-0.89).

|   | SAMPLE | ESC | | | | | iPS | | | Fib | |
|---|---|---|---|---|---|---|---|---|---|---|---|
|   |   | H13 | H14 | H1 | H7 | H9 | SMA-3.5 | SMA-3.6 | WT-4.2 | SMA | WT |
| ESC | H13 | 1 | 0.99 | 0.98 | 0.99 | 0.99 | 0.99 | 0.98 | 0.99 | 0.89 | 0.88 |
|   | H14 | 0.99 | 1 | 0.97 | 0.99 | 0.99 | 0.99 | 0.97 | 0.99 | 0.88 | 0.87 |
|   | H1 | 0.98 | 0.97 | 1 | 0.97 | 0.97 | 0.98 | 0.98 | 0.98 | 0.87 | 0.86 |
|   | H7 | 0.99 | 0.99 | 0.97 | 1 | 0.99 | 0.99 | 0.97 | 0.99 | 0.89 | 0.88 |
|   | H9 | 0.99 | 0.99 | 0.97 | 0.99 | 1 | 0.99 | 0.97 | 0.99 | 0.88 | 0.88 |
| iPS | SMA-3.5 | 0.99 | 0.99 | 0.98 | 0.99 | 0.99 | 1 | 0.98 | 0.99 | 0.89 | 0.88 |
|   | SMA-3.6 | 0.98 | 0.97 | 0.98 | 0.97 | 0.97 | 0.98 | 1 | 0.98 | 0.87 | 0.86 |
|   | WT-4.2 | 0.99 | 0.99 | 0.98 | 0.99 | 0.99 | 0.99 | 0.98 | 1 | 0.89 | 0.88 |
| Fib | SMA | 0.89 | 0.88 | 0.87 | 0.89 | 0.88 | 0.89 | 0.87 | 0.89 | 1 | 0.99 |
|   | WT | 0.88 | 0.87 | 0.86 | 0.88 | 0.88 | 0.88 | 0.86 | 0.88 | 0.99 | 1 |

TABLE 3

Genetic analysis confirms traits of iPS-WT and iPS-SMA cells. DNA fingerprinting of iPS-WT cells showed DNA traits consistent with being derived from Fib-WT cells, and iPS-SMA cells showed DNA characteristics of the Fib-SMA cells.

| Amelogenin | Fib-WT X | iPS-WT X | Fib-SMA X, Y | iPS-SMA X, Y |
|---|---|---|---|---|
| vWA | 14, 16 | 14, 16 | 16, 17 | 16, 17 |
| D8S1179 | 12, 13 | 12, 13 | 10, 12 | 10, 12 |
| TPOX | 8, 11 | 8, 11 | 8 | 8 |
| FGA | 19, 20 | 19, 20 | 20 | 20 |
| D3S1358 | 15, 18 | 15, 18 | 15, 17 | 15, 17 |
| THO1 | 6, 7 | 6, 7 | 6, 7 | 6, 7 |
| D21S11 | 29 | 29 | 29, 30 | 29, 30 |
| D18S51 | 15, 19 | 15, 19 | 15, 17 | 15, 17 |
| Penta E | 16, 18 | 16, 18 | 12, 16 | 12, 16 |
| D5S818 | 12, 13 | 12, 13 | 11, 13 | 11, 13 |
| D13S317 | 11, 12 | 11, 12 | 9, 11 | 9, 11 |
| D7S820 | 10 | 10 | 9, 10 | 9, 10 |
| D16S539 | 11 | 11 | 11, 12 | 11, 12 |
| CSF1PO | 9, 10 | 9, 10 | 9, 10 | 9, 10 |
| Penta D | 9, 12 | 9, 12 | 12 | 12 |

Cells from SMA patients have significantly reduced levels of SMN transcripts that contain all 9 exons (full-length transcripts) due to loss of the SMN1 gene (Lefebvre, S. et al. Identification and characterization of a spinal muscular atrophy-determining gene, Cell 80, 155-165, 1995; Coovert, D. D. et al. The survival motor neuron protein in spinal muscular atrophy Hum. Mol. Genet. 6, 1205-1214, 1997). To test whether the derivation of iPS cells affected SMN production, iPS and fibroblast SMN RNA was analyzed. RT-PCR analysis showed that iPS-WT had comparable SMN levels to the wild-type fibroblasts (Fib-WT), whereas iPS-SMA had lower levels that were similar to the Fib-SMA cells (FIG. 9a). As expected owing to the maintenance of SMN2 function in this disorder (Lefebvre, S. et al. Identification and characterization of a spinal muscular atrophy-determining gene, Cell 80, 155-165, 1995; Coovert, D. D. et al. The survival motor neuron protein in spinal muscular atrophy Hum. Mol. Genet. 6, 1205-1214, 1997), transcripts for some full-length SMN and the alternatively spliced product lacking exon 7 (Δ7) were identified in all samples (FIG. 9a). Furthermore, specific digestion of full-length bands produced the expected SMN2 cleavage products in all samples, confirming that SMN2 produces full-length SMN in both the wild-type and SMA cells (FIG. 9b). Intact SMN1 was detected only in the wild-type cells, thus verifying the absence of SMN1 in SMA cells and recapitulating SMA and carrier transcript patterns (Gavrilov, D. K., Shi, X. Y., Das, K., Gilliam, T. C. & Wang, C. H. Differential SMN2 expression associated with SMA severity, Nature Genet. 20, 230-231, 1998) (FIG. 9b). qRT-PCR further confirmed the significantly reduced level of full-length SMN transcript in SMA cells (61-67% reduced compared to wild-type, FIG. 1). These data are consistent with full-length SMN mRNA levels observed in SMA peripheral blood mononuclear cells (Sumner, C. J. et al. SMN mRNA and protein levels in peripheral blood: biomarkers for SMA clinical trials, Neurology 66, 1067-1073, 2006). Taken together, these data demonstrate that the generation of iPS cells does not alter the critical gene expression profiles or alternative splicing events of SMN1 and SMN2 in unaffected or disease-specific contexts.

Neuronal Differentiation of iPS Cells

To establish whether the lack of SMN1 may affect neuronal differentiation or survival in this new model, we next generated neurons and astrocytes from both iPS-SMA and iPS-WT cells (FIG. 2). Traditional embryoid body formation was found to be very inefficient for neural differentiation from iPS cultures and so an alternate protocol was developed. The iPS cultures were first removed from their feeder layers and grown as floating iPS spheres in a defined medium for a minimum of 2 weeks. These could be continually passaged using a chopping method that avoids losing cell-cell contact known to be important for maintaining both neural and embryonic stem cell proliferation (Fox, V. et al. Cell-cell signaling through NOTCH regulates human embryonic stem cell proliferation, Stem Cells 26, 715-723, 2008; Svendsen, C. N. et al. A new method for the rapid and long term growth of human neural precursor cells, J. Neurosci. Methods 85, 141-152; 1998). These cultures were then dissociated and plated onto laminin-coated coverslips. The iPS-SMA and iPS-WT spheres generated nestin-positive cells indicative of a neural stem cell phenotype (Lendahl, U., Zimmerman, L. B. & McKay, R. D. G. Cns stem-cells express a new class of intermediate filament protein, Cell 60, 585-595; 1990) (FIG. 10A, B). On further differentiation, Tuj1-positive neurons and GFAP-positive astrocytes were also found (FIG. 10C, D). The iPS spheres were simple to expand, remarkably stable over time and maintained the ability to produce neural progeny for more than 20 passages.

As SMA adversely affects motor neurons, we next addressed whether the iPS cells could be lineage-restricted towards a motor neuron fate (FIG. 2). Basing our differentiation model on a previously published report using human embryonic stem cells (Li, X. J. et al. Specification of motoneurons from human embryonic stem cells, Nature Biotechnol. 23, 215-221, 2005), iPS spheres were grown in a neural induction medium containing retinoic acid for 1 week, followed by a further week of retinoic acid and sonic hedgehog (SHH). Spheres were then seeded onto laminin-coated coverslips for another 2-6 weeks (totaling 4-8 weeks of differentiation), and grown in the presence of retinoic acid, SHH, cyclic AMP, ascorbic acid, glial cell line-derived neurotrophic factor and brain-derived neurotrophic factor. One week after plating, long fine processes resembling neuronal axons were observed and neural-like cells were seen migrating out from the sphere. Both iPS-SMA and iPS-WT spheres generated cells that expressed the motor neuron transcription factors HOXB4, OLIG2, ISLET1 (also known as ISL1) and HB9 (Jessell, T. M. Neuronal specification in the spinal cord: Inductive signals and transcriptional codes, Nature Rev. Genet. 1, 20-29, 2000; Wichterle, H., Lieberam, I., Porter, J. A. & Jessell, T. M. Directed differentiation of embryonic stem cells into motor neurons, Cell 110, 385-397, 2002) during the differentiation process (FIG. 10E, F and FIG. 11A-G). The presumptive motor neurons were then immunostained with SMI-32 and choline acetyltransferase (ChAT), which are established markers for mature motor neurons (Carriedo, S. G., Yin, H. Z. & Weiss, J. H. Motor neurons are selectively vulnerable to AMPA/kainate receptor-mediated injury in vitro, J. Neurosci. 16, 4069-4079, 1996). Both SMI-32 and ChAT staining identified positive neurons in all cultures after 4 weeks of differentiation (FIG. 10E-H). At this point there was no significant difference between the iPS-SMA and iPS-WT cultures in the number of motor neurons (12.6%+/−2.2 and 9.5%+/−2.4, respectively) or their size (641.0 mm$^2$+/−81.3 and 669.8 mm$^2$+/−59.1, respectively, FIG. 3A, B) suggesting that iPS-SMA cells are capable of generating motor neurons, which is similar to the human condition and mouse models in which functional motor neurons are generated at early developmental times (Monani, U. R. Spinal muscular atrophy: a deficiency in a ubiquitous protein; a motor neuron-specific disease, Neuron 48, 885-896, 2005).

To develop the system further, we cultured the cells for another 2 weeks and again analyzed motor neuron number and size. Notably, at this time the iPS-SMA cultures had significantly fewer motor neurons (4.3%+/−2.0) with a reduced size (383.1 mm$^2$+/−38.6) compared to the iPS-WT cultures (24.2%+/−4.0, 654.8 mm$^2$+/−32.6, FIG. 3A, B). However, there was no difference in the number of total Tuj1-positive neurons in either iPS-WT or iPS-SMA cells at 6 weeks of differentiation (15.78%+/−2.9 and 15.55%+/−2.8, respectively), suggesting that there is a specific effect of the SMA phenotype on motor neurons. Taken together, these data show that iPS-SMA cells can produce similar numbers of neurons and motor neurons initially, but that the disease phenotype selectively hinders motor neuron production and/or increases motor neuron degeneration at later time points. Although synapses were not observed after 6 weeks of differentiation, by 8 weeks synapses were identified by punctate synapsin staining on iPS-WT SMI-32-positive motor neurons and non-motor neurons (FIG. 10I and FIG. 12), suggesting that pre-synaptic maturation of the neurons was occurring in this system. Notably, synapsin staining remained diffuse on the iPS-SMA SMI-32-positive motor neurons (FIG. 10J), although some punctate synapsin staining was observed on SMI-32 negative cells (FIG. 10J), again suggesting a specific motor neuron deficit in the SMA cultures.

Drug Induced Increase of SMN Protein

Finally, we assessed whether SMN-inducing compounds could increase SMN levels in the iPS-SMA cellular context because this would be an important proof-of-principle for the further development of drug screens. SMN protein is found in both the cytoplasm and nuclear aggregate structures called gems, and the number of gems present is inversely correlated to disease severity (Coovert, D. D. et al. The survival motor neuron protein in spinal muscular atrophy, Hum. Mol. Genet. 6, 1205-1214, 1997). We therefore assessed nuclear gem localization in iPS-SMA- and iPS-WT-derived neurons and astrocytes in the presence or absence of 1 mM valproic acid or 320 mM tobramycin: two compounds shown to increase SMN protein levels (Brichta, L. et al. Valproic acid increases the SMN2 protein level: a well-known drug as a potential therapy for spinal muscular atrophy, Hum. Mol. Genet. 12, 2481-2489, 2003; Sumner, C. J. et al. Valproic acid increases SMN levels in spinal muscular atrophy patient cells, Ann. Neurol. 54, 647-654, 2003; Wolstencroft, E. C., Maths, V., Bajer, A. A., Young, P. J. & Lorson, C. L. Anon-sequence-specific requirement for SMN protein activity: the role of aminoglycosides in inducing elevated SMN protein levels, Hum. Mol. Genet. 14, 1199-1210, 2005). Using an antibody against SMN, untreated Fib-WT and iPS-WT cells showed an abundance of nuclear gems that characterize the normal distribution of this protein (FIG. 13A, C). Both untreated Fib-SMA and iPS-SMA cells showed the expected lack of nuclear gems (FIG. 13B, D) providing further support for reliable disease modeling using iPS-SMA cells. After 2 days of drug treatment, there was no significant increase in gem localization in treated (FIG. 13E, G, I) compared to untreated (FIG. 13C, I) iPS-WT cells. However, valproic acid and tobramycin significantly increased the number of gems in treated compared to untreated iPS-SMA cells (FIG. 13D, F, H, I). We further verified this increase by examining SMN protein by western blot analysis. Two days after drug treatment, total SMN protein was far higher in iPS-WT cells than in iPS-SMA cells (FIG. 13J, K), owing to the lack of SMN1 expression in the latter (FIG. 9B). iPS-SMA cells treated with either valproic acid or tobramycin showed a significant 2- or 3-fold increase, respectively, in SMN protein levels compared to untreated iPS-SMA cells (FIG. 13J, K). We are at present assessing gem formation in differentiating motor neurons and have shown that they can indeed be detected (FIG. 14A, B). Together these data suggest that iPS-SMA cells respond to drug treatment in a similar fashion to Fib-SMA cells and could be useful for new drug screening specifically on motor neurons in future studies.

Previous efforts to understand the mechanisms of SMA in human tissues have relied on fibroblasts from patients or immortalized non-motor neuron cell lines. However, one of the most fascinating aspects of the disease is that a ubiquitous loss of SMN protein from all cells in the body results in the specific degeneration of motor neurons. SMN has been shown to form complexes involved in the production of small nuclear RNA proteins that make up the splicesosome (Pellizzoni, L., Yong, J. & Dreyfuss, G. Essential role for the SMN complex in the specificity of snRNP assembly, Science 298, 1775-1779, 2002; Fischer, U., Liu, Q. & Dreyfuss, G. The SMN-SIP1 complex has an essential role in spliceosomal snRNP biogenesis, Cell 90, 1023-1029, 1997; Liu, Q., Fischer, U., Wang, F. & Dreyfuss, G. The spinal muscular atrophy disease gene product, SMN, and its associated protein SIP1 are in a complex with spliceosomal snRNP proteins, Cell 90, 1013-1021, 1997). More recently, SMN has also been shown to traffic to neuronal processes of motor neurons and may have other important roles in motor axons yet to be fully determined (Carrel, T. L. et al. Survival motor neuron function in motor axons is independent of functions required for small nuclear ribonucleoprotein biogenesis. J. Neurosci. 26, 11014-11022, 2006; Zhang, H. et al., J. Neurosci. 26, 8622-8632; 2006). Using human motor neurons carrying the SMA phenotype generated from a virtually limitless source of iPS cells described here should help to clarify further this new role for SMN in disease initiation and progression.

This is, to our knowledge, the first report to observe disease-specific effects on human motor neuron survival and drug induced increases in protective proteins, thus validating that the iPS model can recapitulate at least some aspects of this genetically inherited disorder. Although the motor neurons generated in the current study show appropriate morphology, specific markers and synapsin staining, experiments are at present underway to more fully assess their function including electrophysiology and co-cultures with muscle fibers. More clones from this and other patient sources also need to be studied. These are important next steps to ensure that the reprogramming has not subtly affected the ability of the motor neurons to function normally. However, this new model should provide a unique platform for studies aimed at both understanding SMA disease mechanisms that lead to motor neuron dysfunction and death, and the potential discovery of new compounds to treat this devastating disorder. It also points to a future in which iPS technology could be used to better understand and develop treatments for several other genetically inherited diseases.

We claim:

1. A method of testing compounds for their ability to modify cellular survival motor neuron (SMN) protein levels comprising the steps of
   (a) obtaining a population of induced pluripotent stem (iPS) cells derived from somatic cells from a spinal muscular atrophy (SMA) patient;
   (b) culturing the cells of step (a) into neurons that maintain an SMA disease genotype and phenotype either before or after exposure to a test compound; and
   (c) examining the effect of the test compound on SMN protein levels, wherein a modification in SMN protein levels in cells exposed to the test compound relative to SMN protein levels in cells that have not been exposed to the test compound indicates that the compound modifies cellular SMN protein levels.

2. The method of claim 1 wherein the exposure to the test compound occurs after the step of culturing the cells into neurons of step (b), and wherein the neurons have an SMN protein level similar (+/−10%) to the SMN protein level of neurons of a spinal muscular atrophy patient.

3. The method of claim 1 wherein step (c) is via examination of nuclear gem localization.

4. The method of claim 2 wherein step (c) is via examination of nuclear gem localization.

5. The method of claim 1 wherein the somatic cells are fibroblasts.

6. A method of evaluating compounds as an SMA therapy comprising the steps of
   (a) obtaining a population of induced pluripotent stem (iPS) cells derived from somatic cells from a spinal muscular atrophy (SMA) patient;
   (b) culturing the cells of step (a) into a cell population comprising motor neurons that maintain an SMA disease genotype and phenotype either before or after exposure to a test compound; and
   (c) examining the effect of the test compound on the survival of motor neurons generated in step (b), wherein the increased survival of motor neurons that have been exposed to the test compound or the increased survival of motor neurons derived from cells exposed to the test compound relative to the survival of motor neurons that have not been exposed to the test compound or motor neurons derived from cells that have not been exposed to the test compound indicates that the compound is a candidate for SMA therapy.

7. The method of claim 6 wherein the exposure to the test compound occurs after the step of culturing the cells into neurons of step (b), and wherein the neurons have an SMN protein level similar (+/−10%) to the SMN protein level of neurons of a spinal muscular atrophy patient.

8. The method of claim 2 wherein the somatic cells are fibroblasts.

* * * * *

UNITED STATES PATENT AND TRADEMARK OFFICE
CERTIFICATE OF CORRECTION

PATENT NO. : 8,211,631 B2  
APPLICATION NO. : 12/653932  
DATED : July 3, 2012  
INVENTOR(S) : Clive Svendsen et al.

It is certified that error appears in the above-identified patent and that said Letters Patent is hereby corrected as shown below:

In the Specification

Column 1, Line 3:  
Please add the following paragraph after the Title:  
--REFERENCE TO GOVERNMENT RIGHTS  
This invention was made with government support under NS057778 awarded by the National Institutes of Health. The government has certain rights in the invention.--.

Signed and Sealed this  
Twenty-ninth Day of December, 2020

Andrei Iancu  
*Director of the United States Patent and Trademark Office*